US012779058B2

(12) United States Patent
Hammoud et al.

(10) Patent No.: US 12,779,058 B2
(45) Date of Patent: Nov. 3, 2026

(54) RADIOLABELED SUGARS FOR IMAGING OF FUNGAL INFECTIONS

(71) Applicant: THE UNITED STATES OF AMERICA, as represented by the Secretary, Department of Health and Human Services, Bethesda, MD (US)

(72) Inventors: Dima A. Hammoud, Bethesda, MD (US); Rolf Eric Swenson, Rockville, MD (US); Xiang Zhang, Bethesda, MD (US); Swati Shah, Bethesda, MD (US); Peter R. Williamson, Bethesda, MD (US); Zhen-Dan Shi, Rockville, MD (US); Falguni Bhattacharyya, Germantown, MD (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 962 days.

(21) Appl. No.: 17/631,600

(22) PCT Filed: Jul. 31, 2020

(86) PCT No.: PCT/US2020/044446
§ 371 (c)(1),
(2) Date: Jan. 31, 2022

(87) PCT Pub. No.: WO2021/025984
PCT Pub. Date: Feb. 11, 2021

(65) Prior Publication Data

US 2022/0273829 A1 Sep. 1, 2022

Related U.S. Application Data

(60) Provisional application No. 62/882,023, filed on Aug. 2, 2019.

(51) Int. Cl.
*A61K 51/04* (2006.01)
*A61P 31/10* (2006.01)
*C07B 59/00* (2006.01)
*C07H 5/02* (2006.01)

(52) U.S. Cl.
CPC .......... *A61K 51/0491* (2013.01); *A61P 31/10* (2018.01); *C07B 59/005* (2013.01); *C07H 5/02* (2013.01); *C07B 2200/05* (2013.01)

(58) Field of Classification Search
CPC ... A61K 51/0491; A61P 31/10; C07B 59/005; C07H 5/02
USPC .......................................................... 424/1.73
See application file for complete search history.

(56) References Cited

U.S. PATENT DOCUMENTS

2014/0314671 A1* 10/2014 Namavari .......... A61K 51/0491 424/1.73
2015/0250906 A1 9/2015 Jain et al.

FOREIGN PATENT DOCUMENTS

JP 2018030823 3/2018
WO WO 2012/125576 9/2012

OTHER PUBLICATIONS

Liu et al. Chem. Eur. J. 2016, 22, 12557-12565. (Year: 2016).*
Wojtusik et al. Chemical Engineering Research and Design 136 (2018) 502-512. (Year: 2018).*

(Continued)

*Primary Examiner* — Michael G. Hartley
*Assistant Examiner* — Sean R Donohue
(74) *Attorney, Agent, or Firm* — Klarquist Sparkman, LLP

(57) ABSTRACT

Disclosed herein are compounds having a structure according to Formula I and optionally Formula IV.

Formula I

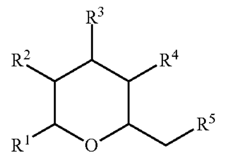

Formula IV

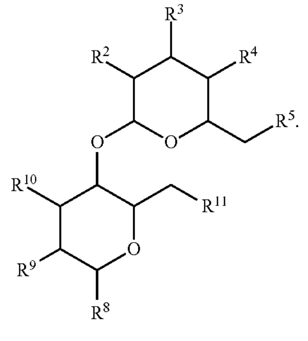

The compounds may be radiolabeled compounds useful for diagnosis and/or imaging fungal infections. In such embodiments, at least one substituent is a radionuclide, such as $^{18}F$. Also disclosed are precursor compounds according to Formula I and/or IV that are useful for making the radiolabeled compounds. In such embodiments, the precursor compound comprises at least one leaving group suitable for introducing a radionuclide, such as $^{18}F$, at a desired position.

Also disclosed are methods for making and using the compounds, including embodiments of a method for imaging and/or diagnosing a fungal infection in a subject.

8 Claims, 9 Drawing Sheets

(56) References Cited

OTHER PUBLICATIONS

McCarter et al. Carbohydrate Res. 249 (1993) 77-90. (Year: 1993).*
Lee et al. Proc. Royal Irish Acad., Section B: Biological, Geological and Chemical Science, 1977, 495-498. (Year: 1977).*
Rana et al. Carbohydrate Res. 1980, 85, 313-317. (Year: 1980).*
Ankrah et al. Curr. Pharmaceutical Des. 2018, 24, 795-805. (Year: 2018).*
Christman et al., The Synthesis of 6-Deoxy-6-18F-a-D-Galactopyranose (XXII), *Journal of Labelled Compounds and Radiopharmaceuticals* XIII(4):555-559, 1977.
International Search Report from International Application No. PCT/US2020/044446 dated Oct. 29, 2020 (8 pages).
Kalita et al., "Arabinofuranose-derived positron-emission tomography radiotracers for detection of pathogenic microorganisms," *Journal of Labelled Compounds and Radiopharmaceuticals* 63:231-239, 2020.
Neal et al., "Synthesis of [$^{18}$F]-6-deoxy-6-fluoro-D-glucose ([$^{18}$F]6FDG), a potential tracer of glucose transport," *Journal of Labelled Compounds and Radiopharmaceuticals* 48:845-854, 2005.
Written Opinion from International Application No. PCT/US2020/044446 dated Oct. 29, 2020 (11 pages).
Buffo et al., "Cellulolytic enzymes production guided by morphology engineering," *Enzyme and Microbial Technology*, 149:109833, 8 pages (Sep. 2021) Available online May 26, 2021.
Chen et al., "Purification and characterization of a novel β-glucosidase from *Aspergillus flavus* and its application in saccharification of soybean meal," *Preparative Biochemistry and Biotechnology*, 49(7):671-678 (Apr. 16, 2019).
De Morais et al., "Catalytic and thermodynamic properties of β-glucosidases produced by *Lichtheimia corymbifera* and *Byssochlamys spectabilis," Preparative Biochemistry and Biotechnology*, 48(9):777-786 (Oct. 10, 2018).
Dos Reis et al., "Identification and characterization of putative xylose and cellobiose transporters in *Aspergillus nidulans," Biotechnol Biofuels*, 9:204, 19 pages (Sep. 26, 2016).
El-Naggar et al., "Optimization of β-Glucosidase Production by *Aspergillus terreus* Strain EMOO 6-4 Using Response Surface Methodology Under Solid-State Fermentation," *Preparative Biochemistry & Biotechnology*, 45(6):568-587 (Nov. 11, 2014).
Garcia et al., "Production of β-glucosidase on solid-state fermentation by *Lichtheimia ramosa* in agroindustrial residues: Characterization and catalytic properties of the enzymatic extract," *Electronic Journal of Biotechnology*, 18(4):314-319 (Jul. 2015) available online Jun. 27, 2015.
Huang et al., "Identification of a β-glucosidase from the *Mucor circinelloides* genome by peptide pattern recognition," *Enzyme and Microbial Technology*, 67:47-52 (Dec. 2014) available online Sep. 16, 2014.
Kwon et al., "Purification and characterization of two extracellular β-glucosidases from *Aspergillus nidulans," FEMS Microbiology Letters*, 97(1-2):149-153 (Oct. 1992).
Losada et al., "Compatible traits of oleaginous Mucoromycota fungi for lignocellulose-based simultaneous saccharification and fermentation," *Biotechnology for Biofuels and Bioproducts*, 18:24, 15 pages (Feb. 24, 2025).
Namnuch et al., "Lignocellulose hydrolytic enzymes production by *Aspergillus flavus* KUB2 using submerged fermentation of sugarcase bagasse waste," *Mycology*, 12(2):119-127 (Aug. 18, 2020).
Narendra Kumar et al., "Bioethanol production by enzymatic hydrolysis from *Aspergillus calidoustus* employing different lignocellulosic wastes," *Biocatalysis and Agricultural Biotechnology*, 53:102847, 12 pages (Oct. 2023) available online Sep. 20, 2023.
Pel et al., "Genome sequencing and analysis of the versatile cell factory *Aspergillus niger* CBS 513.88," *Nature Biotechnology*, 25(2):221-231 (Feb. 2007) available online Jan. 28, 2007.
Sorensen et al., "Fungal Beta-Glucosidases: A Bottleneck in Industrial Use of Lignocellulosic Materials," *Biomolecules*, 3(3):612-631 (Sep. 3, 2013).
Wei et al., "Genomic, Proteomic, and Biochemical Analyses of Oleaginous *Mucor circinelloides*: Evaluating Its Capability in Utilizing Cellulolytic Substrates for Lipid Production," 8(9):e71068, 12 pages (Sep. 4, 2013).
Yan et al., "Characterization of β-glucosidase from *Aspergillus terreus* and its application in the hydrolysis of soybean isoflavones," *Journal of Zhejiang University—Science B* (*Biomedicine & Biotechnology*), 17(6):455-464 (Jun. 10, 2016).

* cited by examiner

A.fumigatus
Uptake (pmol/mg)
0
10
20
30
40
30
60
120
Time (minutes)

E.coli
Uptake (pmol/mg)
0
20
40
60
80
100
30
60
120
Time (minutes)
1 2-DG
2 L-rhamnose In vitro Aspergillus uptake 3H-Cellobiose pmol/g
20000
15000
10000
5000
0
30min
60min
120min
2
1
1 2-Deoxyglucose
2 Cellobiose In vitro uptake in mammalian cells pmol/g
250
200
150
100
50
0
-50
10min
30min
120min
1
2
1 2-Deoxyglucose
2 Cellobiose

RADIOLABELED SUGARS FOR IMAGING OF FUNGAL INFECTIONS

CROSS REFERENCE TO RELATED APPLICATION

This is the U.S. National Stage of International Application No. PCT/US2020/044446, filed Jul. 31, 2020, which was published in English under PCT Article 21(2), which in turn claims the benefit of the earlier filing date of U.S. provisional patent application No. 62/882,023, filed Aug. 2, 2019. The provisional application is incorporated herein in its entirety.

FIELD

Provided herein are radiolabeled sugars, such as [$^{18}$F]-rhamnose and [$^{18}$F]-cellobiose, and methods of their use to detect and monitor a fungal infection.

BACKGROUND

Fungal infections remain a major health burden with very high mortality and morbidity in immunosuppressed cancer and stem cell transplant patients, in advanced HIV disease and in some congenital immunodeficiencies. A recent report estimated global mortality from fungal disease to be >1.6 million, similar to that of tuberculosis and >3-fold that of malaria (Bongomin et al., J Fungi (Basel), 3, 2017). Yet, despite the magnitude of the problem, there are currently no clinically-available fungal-specific imaging agents. FDG PET is a nonspecific technique that can be used for imaging patients with suspected active fungal infections. It cannot however, differentiate between infection and inflammation, between the various fungal pathogens or differentiate fungi from other pathogens such as bacteria. The development of fungus-specific imaging has been attempted using varying approaches including targeted antibodies (Rolle et al., Proc Natl Acad Sci USA, 113:E1026-3, 2016), 99mTc labeled MORF oligomers targeting fungal ribosomal RNA (rRNA) (Wang et al., Nucl Med Biol, 40:89-96, 2013), and the use of radiolabeled siderophores (Haas et al., PLoS Pathog, 11: e1004568, 2015). Many of those ligands however are still in early stages of development, have been abandoned or mostly, have not been tested in humans. Thus, new fungal-specific imaging ligands are needed.

SUMMARY

Provided herein are new fungal-specific imaging ligands, which exploit metabolic pathways that are selectively expressed by fungi, but not by mammalian cells or bacteria. These fungal-specific imaging ligands can be used to diagnose and/or monitor a fungal infection in vivo, without the need for invasive procedures or biopsies.

Disclosed herein are compounds having a formula I

Formula I

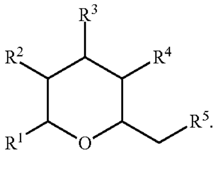

With respect to Formula I, $R^1$ is a radionuclide, OH, $OR^6$, $OR^7$ or X. X is

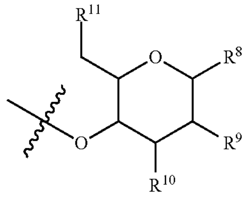

where each of $R^7$, $R^8$, $R^9$ and $R^{19}$ independently is a radionuclide, OH, $OR^6$, or $OR^7$. Each of $R^2$, $R^3$ and $R^4$ independently is OH, $OR^6$, $OR^7$ or a radionuclide. $R^5$ is H, OH, $OR^6$, $OR^7$ or a radionuclide, with the provision that when $R^1$ is X then $R^5$ is OH, $OR^6$, $OR^7$ or a radionuclide, and when $R^1$ is other than X, then $R^5$ is H, $OR^7$, or a radionuclide. $R^6$ is acetyl, formyl, methoxyacetyl, benzoyl, haloacetyl or trialkylsilyl, and in some embodiments, $R^6$ is acetyl. And $R^7$ is triflate, mesylate or tosylate, and in some embodiments, $R^7$ is triflate.

Also with respect to Formula I, one of the following conditions (a) or (b) applies:

(a) if $R^1$ is X then either at least one of $R^2$-$R^5$ and $R^8$-$R^{11}$ is a radionuclide and the rest are OH, or at least one of $R^2$-$R^5$ and $R^8$-$R^{11}$ is $OR^7$ and the rest are $OR^6$; and (b) if $R^1$ is other than X, then at least one of $R^1$-$R^5$ and $R^8$-$R^{11}$ is a radionuclide and the rest are OH except for $R^5$ which is either a radionuclide or H, or at least one of $R^1$-$R^5$ and $R^8$-$R^{11}$ is $OR^7$ and the rest are $OR^6$ except for $R^5$ which is either $OR^7$ or H.

In any embodiments, the radionuclide may be $^{18}$F.

In some embodiments, $R^1$ is $^{18}$F, OH, $OR^6$, or $OR^7$ and condition (b) applies. In such embodiments, each of $R^1$, $R^2$, $R^3$, and $R^4$ independently may be $^{18}$F or OH; $R^5$ may be $^{18}$F or H; and at least one of $R^1$-$R^5$ may be $^{18}$F. And in some embodiments, $R^1$ is $^{18}$F, $R^2$-$R^4$ are OH, and $R^5$ is H; $R^2$ is $^{18}$F, $R^1$, $R^3$ and $R^4$ are OH, and $R^5$ is H; $R^3$ is $^{18}$F, $R^1$, $R^2$ and $R^4$ are OH, and $R^5$ is H; $R^4$ is $^{18}$F, $R^1$, $R^2$ and $R^3$ are OH, and $R^5$ is H; or $R^5$ is $^{18}$F, and $R^1$-$R^4$ are OH. Additionally, or alternatively, the compound may have a Formula II Formula II

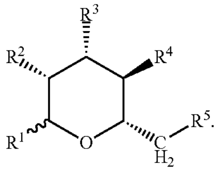

And with respect to Formula II, the compound may be

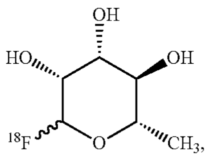

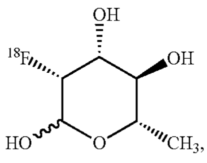

-continued

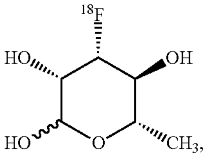

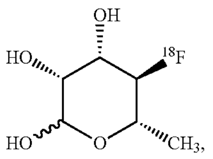

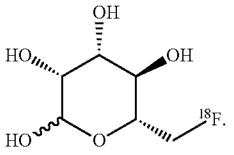

In other embodiments, each of $R^1$, $R^2$, $R^3$, and $R^4$ independently is $OR^6$ or $OR^7$; $R^5$ is $OR^7$ or H; and at least one of $R^1$-$R^5$ is $OR^7$. In some such embodiments, one of $R^1$-$R^5$ is $OR^7$ and the rest are $OR^6$. And/or in some embodiments, the compound has a formula selected from III-a

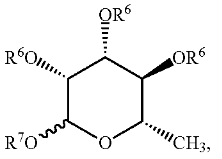

III-b

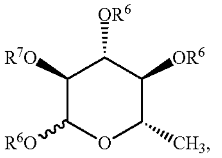

III-c

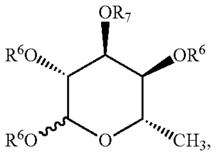

III-d

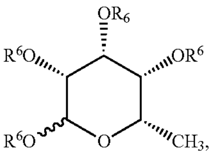

or

III-e

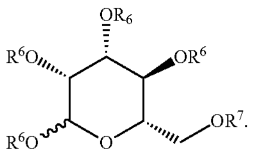

Additionally, in some embodiments, $R^1$ is $OR^7$, $R^2$-$R^4$ are $OR^6$, and $R^5$ is H; $R^2$ is $OR^7$, $R^1$, $R^3$ and $R^4$ are $OR^6$, and $R^5$ is H; $R^3$ is $OR^7$, $R^1$, $R^2$ and $R^4$ are $OR^6$, and $R^5$ is H; $R^4$ is $OR^7$, $R^1$, $R^2$ and $R^3$ are $OR^6$, and $R^5$ is H; or $R^5$ is $OR^7$, and $R^1$-$R^4$ are $OR^6$. And $R^6$ may be acetyl and $R^7$ may be triflate.

In other embodiments of Formula I, the compound has a structure according to Formula IV and condition (a) applies Formula IV

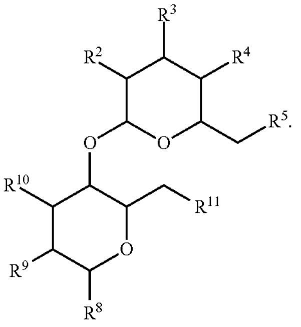

In some such embodiments, each of $R^2$-$R^5$ and $R^8$-$R^{11}$ independently is $^{18}F$ or OH, and at least one of $R^2$-$R^5$ and $R^8$-$R^{11}$ is $^{18}F$, and in certain embodiments, one of $R^2$-$R^5$ and $R^8$-$R^{11}$ is $^{18}F$ and the rest of $R^2$-$R^5$ and $R^8$-$R^{11}$ are OH.

Additionally or alternatively, the compound may have a structure according to Formula V Formula V

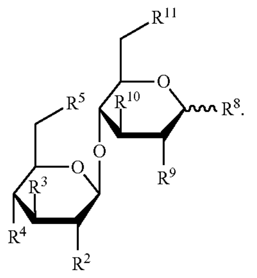

With respect to Formula V, in some embodiments, $R^2$ is $^{18}F$ and $R^3$-$R^5$ and $R^8$-$R^{11}$ are OH; $R^3$ is $^{18}F$ and $R^2$, $R^4$, $R^5$ and $R^8$-$R^{11}$ are OH; $R^4$ is $^{18}F$ and $R^2$, $R^3$, $R^5$ and $R^8$-$R^{11}$ are OH; $R^5$ is $^{18}F$ and $R^2$-$R^4$ and $R^8$-$R^{11}$ are OH; $R^8$ is $^{18}F$ and $R^2$-$R^5$ and $R^9$-$R^{11}$ are OH; $R^9$ is $^{18}F$ and $R^2$-$R^5$ and $R^8$, $R^{10}$ and $R^{11}$ are OH; $R^{10}$ is $^{18}F$ and $R^2$-$R^5$ and $R^8$, $R^9$ and $R^{11}$ are OH; or $R^{11}$ is $^{18}F$ and $R^2$-$R^5$ and $R^8$-$R^{10}$ are OH. In certain embodiments, $R^9$ is $^{18}F$ and $R^2$-$R^5$ and $R^8$, $R^{10}$ and $R^{11}$ are OH, but in other embodiments, $R^2$ is $^{18}F$ and $R^3$-$R^5$ and $R^8$-$R^{11}$ are OH.

In other embodiments of Formula IV, each of $R^2$-$R^5$ and $R^8$-$R^{11}$ independently is $OR^6$ or $OR^7$, and at least one of $R^2$-$R^5$ and $R^8$-$R^{11}$ is $OR^7$. In some embodiments, one of $R^2$-$R^5$ and $R^8$-$R^{11}$ is $OR^7$ and the rest of $R^2$-$R^5$ and $R^8$-$R^{11}$ are $OR^6$. And in certain embodiments, $R^2$ is $OR^7$ and $R^3$-$R^5$ and $R^8$-$R^{11}$ are $OR^6$; $R^3$ is $OR^7$ and $R^2$, $R^4$, $R^5$ and $R^8$-$R^{11}$ are $OR^6$; $R^4$ is $OR^7$ and $R^2$, $R^3$, $R^5$ and $R^8$-$R^{11}$ are $OR^6$; $R^5$ is $OR^7$ and $R^2$-$R^4$ and $R^8$-$R^{11}$ are $OR^6$; $R^8$ is $OR^7$ and $R^2$-$R^5$ and $R^9$-$R^{11}$ are $OR^6$; $R^9$ is $OR^7$ and $R^2$-$R^5$ and $R^8$, $R^{10}$ and $R^{11}$ are $OR^6$; $R^{10}$ is $OR^7$ and $R^2$-$R^5$ and $R^8$, $R^9$ and $R^{11}$ are $OR^6$; or $R^{11}$ is $OR^7$ and $R^2$-$R^5$ and $R^8$-$R^{10}$ are $OR^6$. And $R^6$ may be acetyl and $R^7$ may be triflate.

Also provided are compositions that include one or more radiolabeled compounds and a pharmaceutically acceptable carrier, such as water or saline.

Also provided are methods of using the disclosed radiolabeled compounds to detect a fungus, in vivo to diagnose and/or monitor a fungal infection in a subject.

The foregoing and other objects and features of the disclosure will become more apparent from the following detailed description, which proceeds with reference to the accompanying figures.

BRIEF DESCRIPTION OF THE DRAWINGS

(FIG. 1E) In vitro uptake of $^{18}F$-rhamnose in live and heat killed *A. fumigatus* and *E. coli*. (FIG. 1F) Representative autoradiography images of in vivo uptake of $^{3}H$-rhamnose in the lungs of healthy, poly (I:C) treated (sterile inflammation) and *A. fumigatus* infected mice is shown in the top panels. Bright field images of the respective lung sections are in the bottom panel.

(FIG. 3A) Representative dynamic [$^{18}F$]-rhamnose PET images, averaged from 520-3520 seconds post injection. Increased uptake is seen in the lungs of nasopharyngeally-infected pulmonary IA (AF NP) mice while no appreciable uptake is seen in the lungs of control or sterile lung (poly (I:C) inflammation mice. The first 520 seconds were removed from analysis to reduce potential effects of increased vascularity after injection. (FIG. 3B) Time activity curve of [$^{18}F$]-rhamnose uptake in control, poly (I:C), and AF NP models from 0-3370 seconds post [$^{18}F$]-rhamnose injection.

(FIG. 4C) Biodistribution studies show increased activity in the lungs of infected mice compared to control animals Increased activity in the brain may reflect free labeled glucose following hydrolysis of cellobiose with secondary uptake by the brain.

DETAILED DESCRIPTION

I. Terms

Figures 1A, 1B:
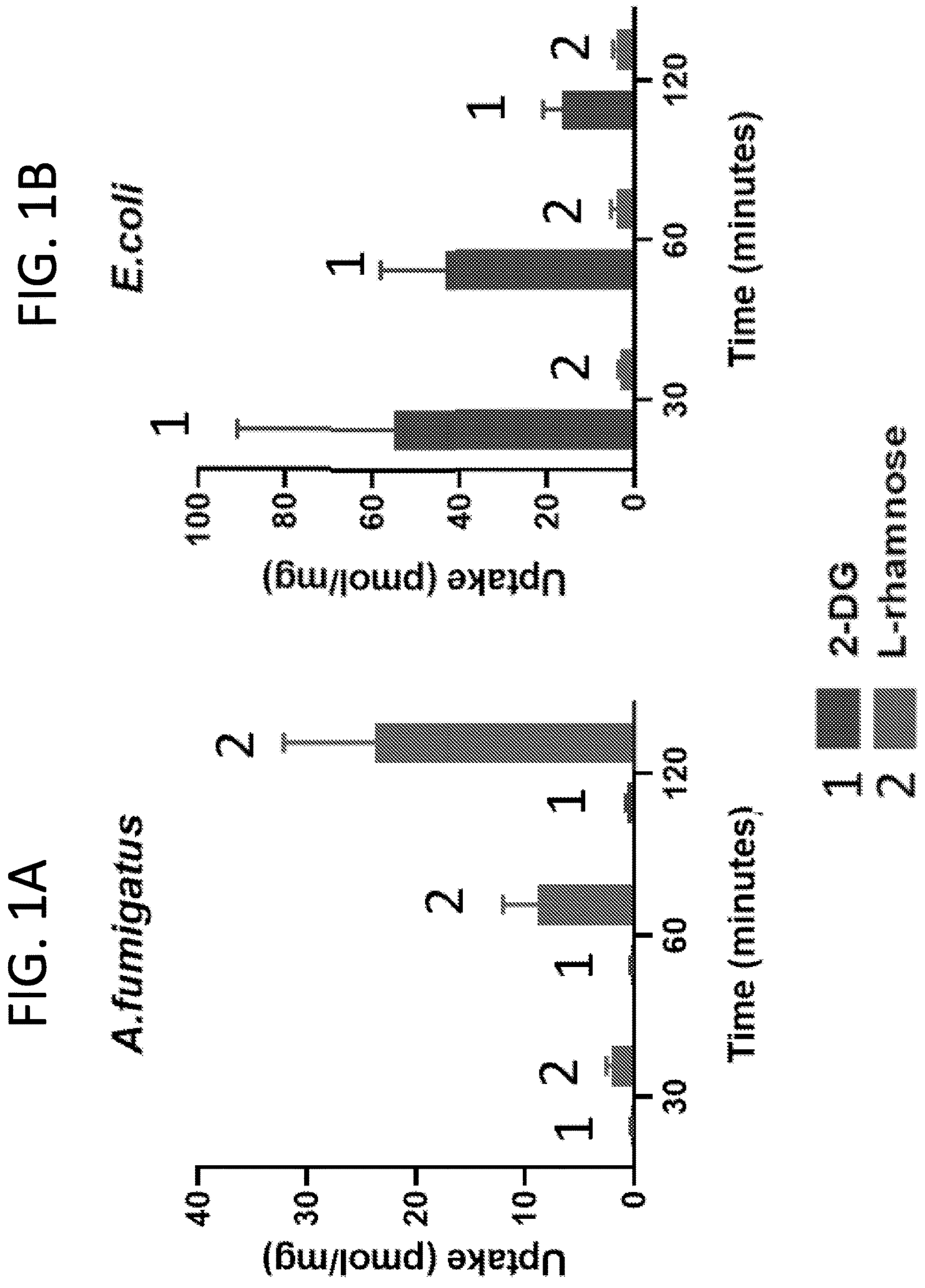
FIGS. 1A-1F. in vitro uptake of $^{3}H$-2-deoxyglucose (2-DG) and $^{3}H$-rhamnose in (FIG. 1A) *A. fumigatus* (FIG. 1B) *E. coli* (FIG. 1C) *S. aureus* and (FIG. 1D) J774 macrophages at various time-points. The net uptake of live cultures are plotted in the graphs after subtracting the background uptake by heat-killed cultures (except J774 macrophages where only uptake in live cultures was measured).

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

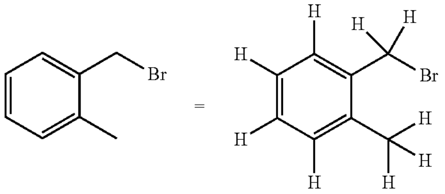

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

Administration: To provide or give a subject an agent, such as a radiolabeled sugar provided herein and/or an anti-fungal agent, by any effective route. Exemplary routes of administration include, but are not limited to, topical, injection (such as subcutaneous, intramuscular, intradermal, intraperitoneal, intraosseous, intra-arterial, and intravenous), oral, ocular, sublingual, rectal, transdermal, intranasal, vaginal and inhalation routes.

Alkyl: A saturated aliphatic hydrocarbyl group having from 1 to 25 ($C_{1-25}$) or more carbon atoms, more typically 1 to 10 ($C_{1-10}$) carbon atoms such as 1 to 6 ($C_{1-6}$) carbon atoms or 1 to 4 ($C_{1-4}$) carbon atoms. This term includes, by way of example, linear and branched hydrocarbyl groups such as methyl ($CH_3$), ethyl ($—CH_2CH_3$), n-propyl ($—CH_2CH_2CH_3$), isopropyl ($—CH(CH_3)_2$), n-butyl ($—CH_2CH_2CH_2CH_3$), isobutyl ($—CH_2CH_2(CH_3)_2$), sec-butyl ($—CH(CH_3)(CH_2CH_3)$, or t-butyl ($—C(CH_3)_3$).

Contact: Placement in direct physical association, including a solid or a liquid form. Contacting can occur in vitro or ex vivo, for example, by adding a reagent to a sample, or in vivo by administering to a subject.

Detect or measure: To determine if a particular agent (e.g., fungal infection, radiolabeled sugar provided herein) is present or absent, and in some examples further includes semi-quantification or quantification of the agent if detected.

Effective amount: An amount of a composition that alone, or together with an additional therapeutic agent(s) sufficient to achieve a desired effect, for example in vivo The effective amount of the agent (such as an anti-fungal agent) can be dependent on several factors, including, but not limited to the subject being treated (e.g., whether the subject is immune compromised), the severity, stage, and type of fungal infection being treated, the particular therapeutic agent, and the manner of administration. Effective amounts also can be determined through various in vitro, in vivo or in situ immunoassays. One or more anti-fungal agents can be administered in a single dose, or in several doses, as needed to obtain the desired response.

In one example, an effective amount or concentration is one that is sufficient to treat a fungal infection in a subject, for example by reducing or inhibiting one or more symptoms associated with the infection. The infection and symptoms need not be completely eliminated for the method to be effective. For example, administering one or more anti-fungal agents to a subject can substantially decrease the fungal infection (or one or more signs or symptoms of the infection) in the subject, such as a decrease of at least 20%, at least 50%, at least 80%, at least 90%, at least 95%, at least 98%, or even at least 100%, as compared to the amount present prior to administration of the ng one or more anti-fungal agents.

Fungus: A member of the group of eukaryotic organisms that includes chitin in their cell walls. Includes fungal organisms that can infect a subject, such as mammals and birds. Fungal infections invade one or more tissues causing infection, for example in the skin or internal organs such as the blood, kidney, heart, esophagus, lungs, sinuses, gastro-intestinal tract, and central nervous system (e.g., brain, spinal cord). Exemplary fungi that can be diagnosed or treated using the methods provided herein include, but are not limited to, *Aspergillus* (which can cause Aspergillosis), such as *A. fumigatus, A. flavus, A. terreus*, and *A. niger; Candida* (which can cause candidiasis), such as *C. albicans; Cryptococcus* (which can cause Cryptococcosis), such as *C. neoformans* and *C. gattii*; and Mucormycetes (which can cause mucormycosis, sometimes called zygomycosis), such as *Rhizopus* species, *Mucor* species, *Rhizomucor* species, *Syncephalastrum* species, *Cunninghamella bertholletiae, Apophysomyces* species, and *Lichtheimia* (formerly *Absidia*).

Halo: Fluoro, chloro, bromo or iodo.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, PA, 19th Edition (1995), describes compositions and formulations suitable for pharmaceutical delivery of one or more therapeutic compounds, such as one or more radiolabeled compounds provided herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Precursor and precursor compound: Compounds that are used to make a radiolabeled compound, but typically do not comprise a radionuclide themselves. A person of ordinary skill in the art understands that because transport of radioactive compounds may be problematic, due to transport restrictions and that fact that the radioactive isotope decays over time, the precursor compound may be prepared, stored and/or transported, and the radionuclide is added prior to use, such as by an end user. Typically, a precursor compound comprises a leaving group that can exchanged or displaced when the radionuclide is introduced. The precursor compound also may comprise one or more protecting groups that protect other functional groups when the radionuclide is introduced, and can be removed prior to use.

Radiolabeled: A compound that comprises a radionuclide.

Radionuclide: A radioactive isotope. For example, $^{18}F$ is a radionuclide of fluorine.

Sample: A sample of biological material obtained from a subject, which can include cells (such as fungal cells), proteins, nucleic acid molecules (such as DNA and/or RNA). Biological samples include all clinical samples useful for detection of disease, such as a fungal infection, in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, stool/feces, saliva, sputum, urine, bronchoalveolar lavage, cerebrospinal fluid (CSF), nasal swabs, etc.), or fine-needle aspirates. Samples may be used directly from a subject, or may be processed before analysis (such as concentrated, diluted, purified). In a particular example, a sample or biological sample is obtained from a subject having, suspected of having, or at risk of having a fungal infection.

Subject or patient: A term that includes human and non-human mammals. In one example, the subject is a human or veterinary subject, such as a mouse, non-human primate, cow, pig, rabbit, rat, horse, cat, dog, and the like. In some examples, the subject is a mammal (such as a human) who has a fungal infection, or is being treated for a fungal infection. In some examples, the subject is immune compromised. In some examples, the subject is immune compromised and has a fungal infection, such as invasive aspergillosis.

In some examples, a subject analyzed with the disclosed methods is one who has received a transplant (e.g., transplant of at least one of a stem cell or solid organ, such as lung, heart, liver, kidney, pancreas, or intestine). In some examples, a subject analyzed with the disclosed methods is one who has a primary immunodeficiency (examples of primary immunodeficiency diseases include those listed in Al-Herz et al. (Frontiers in Immunology, volume 5, article 162, Apr. 22, 2014, herein incorporated by reference in its entirety), e.g., T-B+ SCID, T-B− SCID, WHIM syndrome, IL-7 receptor severe combined immune deficiency (SCID), Adenosine deaminase deficiency (ADA) SCID, Purine nucleoside phosphorylase (PNP) deficiency, Wiskott-Aldrich syndrome (WAS), Chronic granulomatous disease (CGD), Leukocyte adhesion deficiency (LAD), Duchenne muscular dystrophy, Glycogen storage disease type IA, Retinal Dystrophy, and X-linked immunodeficiency with magnesium defect, Epstein-Barr virus infection, and neoplasia (XMEN)). In some examples, a subject analyzed with the disclosed methods is one who has HIV or AIDS. In some examples, a subject analyzed with the disclosed methods is one who has cancer, such as a cancer of the lung, liver, pancreas, breast, prostate, ovary, colon, rectum, head and neck, brain, bone, or blood.

The terms "$^{18}$F-rhamnose" and "[$^{18}$]-rhamnose" include $^{18}$F-labeled rhamnose and deoxyrhamnose analogs, such as, but not limited to, 6-$^{18}$F-rhamnose and $^{18}$F-deoxyrhamnose analogs where the $^{18}$F is at the 1, 2, 3, 4, or 5 position.

The term "$^{18}$F-cellobiose" and "[$^{18}$F]-cellobiose" include $^{18}$F-labeled cellobiose and deoxycellobiose analogs, such as, but not limited to, 6-$^{18}$F-cellobiose, 12-$^{18}$F-cellobiose, and $^{18}$F-deoxycellobiose analogs where the $^{18}$F is at the 1, 2, 3, 8, 9, or 10 positions.

II. Overview

The inventors identified sugars and other molecules involved in the metabolic pathways of clinically-relevant fungal infections, and generated radiolabeled versions (3H or 14C) that were tested for in vitro uptake in bacteria (gram-negative, gram-positive, *Pseudomonas aeruginosa*), macrophages (J774 cell line) and m clinically-relevant fungal strains including *Aspergillus, Rhizomucor, Cryptococcus* and *Candida albicans*. Organisms and cells were exposed to the radiolabeled compounds and the in vitro uptake was measured (retained radioactivity after incubation and washing of the cultures measured using a beta counter). If positive uptake in the fungi was observed with no or only low uptake in bacteria and mammalian cells, organ biodistribution studies and autoradiography were used to determine specific uptake in different animal models of fungal infection. For the biodistribution and autoradiography studies showing specific uptake of the radioactive molecules by fungal-infected animals (i.e., retained radioactivity in the lungs in the infected animals but not in the control animals), the ligand(s) specific for each type of fungi was radiolabeled with 18F or other PET isotopes. Using the radiolabeled ligand(s), live PET imaging is performed on infected mice using a microPET/CT scanner. This is done by injecting the radioactive ligand intravenously through the tail vein and then positioning the animals inside the microPET/CT gantry and obtaining CT scan images as well as PET emission data. The images are reconstructed and analyzed using special software. To confirm specificity for fungal infection, in vivo uptake of the ligand(s) in animal models of sterile inflammation, as well as models of bacterial infection (gram positive and gram negative bacteria) are performed.

Three main mouse models were developed: (1) *Aspergillus* lung infection (nasopharyngeal administration of 30 μl suspension of *Aspergillus conidia*), (2) *Aspergillus* hematogenous spread (intravenous administration of 100 μl of fungal suspension via the tail vein) and (3) sterile lung inflammation model (induced by nasopharyngeal administration of 50-100 μg of poly (I:C) suspension in 30 μl of sterile PBS; poly(I:C) is a synthetic double stranded RNA which activates Toll-like receptors-3 (TLR3), thereby inducing signaling via multiple inflammatory pathways).

Additional mouse models included Gram negative (*E. coli*) and gram positive (*S. aureus*) bacterial infection models (myositis induced by injection of 107-109 CFU of *E. coli* or *Staphylococcus aureus* intramuscularly into the caudal thigh region (hind limb)), a model of subcutaneous *Aspergillus* infection (200 μl suspension containing 5×105 to 5×107 conidia injected subcutaneously, in the right dorsum) and a model of contralateral sterile inflammation (heat killed conidia+complete Freund's adjuvant (CFA)).

Other fungal mouse models besides *Aspergillus* include *Candida albicans* (intravenous injection of 100-150 μl of *Candida* culture containing a CFU of 103-109) and *Cryptococcus neoformans* (30 μl suspension of fungal cells administered through the posterior pharyngeal method) infected models.

Two sugars, L-rhamnose and cellobiose were radiolabeled and can be used as PET ligands.

III. Compounds

Disclosed herein are radiolabeled compounds and precursors thereof. Radiolabeled compounds comprise a radionuclide, for example $^{18}$F. The radiolabeled compounds are useful as for diagnosing certain infections, such as fungal infections, in a patient. In some embodiments, the compounds are analogs and/or derivatives of sugars that are metabolized by fungi, and may be selectively metabolized by the fungi, such that the patient does not substantially metabolize the sugar. This results in the radiolabeled metabolites selectively accumulating in the fungi, thereby identifying the fungal infection.

In some embodiments, the compound has a formula I

Formula I

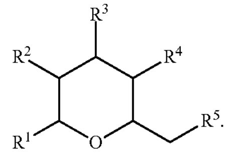

With respect to Formula I:

$R^1$ is a radionuclide, OH, $OR^6$, $OR^7$ or X;

X is

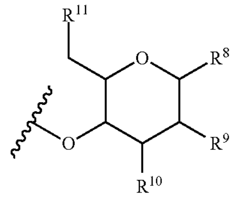

where each of $R^7$, $R^8$, $R^9$ and $R^{10}$ independently is a radionuclide, OH, $OR^6$, or $OR^7$;

each of $R^2$, $R^3$ and $R^4$ independently is OH, $OR^6$, $OR^7$ or a radionuclide;

$R^5$ is H, OH, $OR^6$, $OR^7$ or a radionuclide, with the proviso that when $R^1$ is X then $R^5$ is OH, $OR^6$, $OR^7$ or a radionuclide, and when $R^1$ is other than X, (i.e., $R^1$ is a radionuclide, OH, $OR^6$, $OR^7$) then $R^5$ is H, $OR^7$, or a radionuclide;

$R^6$ is a suitable protecting group, and may be an ester or silyl protecting group, such as acetyl ($CH_3C({=}O)$—; Ac), formyl, methoxyacetyl, benzoyl, haloacetyl (such as trifluoroacetyl, chloroacetyl, dichloroacetyl, or trichloroacetyl) or trialkylsilyl (such as trimethyl silyl or triethyl silyl), and in certain embodiments, $R^6$ is acetyl;

$R^7$ is a suitable leaving group, such as triflate ($CF_3SO_2$; Tr), mesylate ($CH_3SO_2$) or tosylate ($CH_3PHSO_2$), and in certain embodiments, $R^7$ is triflate;

Also, with respect to Formula I the following conditions apply:

(a) if $R^1$ is X then either at least one of $R^2$-$R^5$ and $R^8$-$R^{11}$ is a radionuclide and the rest are OH, or at least one of $R^2$-$R^5$ and $R^8$-$R^{11}$ is $OR^7$ and the rest are $OR^6$; and (b) if $R^1$ is other than X, then at least one of $R^1$-$R^5$ and $R^8$-$R^{11}$ is a radionuclide and the rest are OH except for $R^5$ which is either a radionuclide or H; or at least one of $R^1$-$R^5$ and $R^8$-$R^{11}$ is $OR^7$ and the rest are $OR^6$ except for $R^5$ which is either $OR^7$ or H.

In some embodiments, $R^1$ is $OR^6$, $OR^7$, X; each $R^2$-$R^4$ independently is $OR^6$ or $OR^7$; $R^5$ is H, $OR^6$ or $OR^7$; and, if present, each of $R^7$, $R^8$, $R^9$ and $R^{10}$ independently is $OR^6$ or $OR^7$.

In other embodiments, $R^1$ is OH, a radionuclide, or X; each $R^2$-$R^4$ independently is OH or a radionuclide; $R^5$ is H, OH or a radionuclide; and, if present, each of $R^7$, $R^8$, $R^9$ and $R^{10}$ independently is OH or a radionuclide.

In any embodiments, the radionuclide may be $^{18}F$.

I. Rhamnose Analogs

In some embodiments of Formula I, the compound is a rhamnose analog. In such embodiments, $R^1$ is other than X, i.e., $R^1$ is a radionuclide, OH, $OR^6$, or $OR^7$ and condition (b) applies. In any embodiments, the rhamnose analog may be an L-Rhamnose analog.

i) Radiolabeled Rhamnose

In some embodiments, the rhamnose analog is a radiolabeled analog, such as an $^{18}F$ radiolabeled rhamnose or deoxyrhamnose analog. In such embodiments, each of $R^1$, $R^2$, $R^3$, and $R^4$ independently is $^{18}F$ or OH, and $R^5$ is $^{18}F$ or H, where at least one of $R^1$-$R^5$ is $^{18}F$. In some embodiments, one of $R^1$-$R^5$ is $^{18}F$.

In some embodiments, the compound is $^{18}F$ radiolabeled L-Rhamnose analog and has a structure according to Formula II:

Formula II

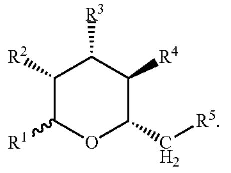

With respect to Formula II, $R^1$-$R^4$ are $^{18}F$ or OH and $R^5$ is $^{18}F$ or H, where at least one, and optionally exactly one of $R^1$-$R^5$ is $^{18}F$.

In an embodiment of Formulas I or II, $R^1$ is $^{18}F$, $R^2$-$R^4$ are OH, and $R^5$ is H.

In an embodiment of Formulas I or II, $R^2$ is $^{18}F$, $R^1$, $R^3$ and $R^4$ are OH, and $R^5$ is H.

In an embodiment of Formulas I or II, $R^3$ is $^{18}F$, $R^1$, $R^2$ and $R^4$ are OH, and $R^5$ is H.

In an embodiment of Formulas I or II, $R^4$ is $^{18}F$, $R^1$, $R^2$ and $R^3$ are OH, and $R^5$ is H.

In an embodiment of Formulas I or II, $R^5$ is $^{18}F$, and $R^1$-$R^4$ are OH.

In a particular embodiment of Formula II, $R^2$ is $^{18}F$, $R^1$, $R^3$ and $R^4$ are OH, and $R^5$ is H; or $R^3$ is $^{18}F$, $R^1$, $R^2$ and $R^4$ are OH, and $R^5$ is H; or $R^5$ is $^{18}F$, and $R^1$-$R^4$ are OH.

Exemplary Rhamnose analogs according to Formula II:

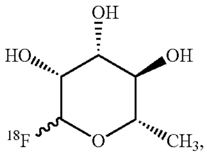,
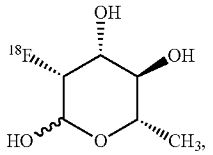,
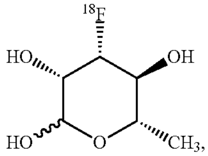,
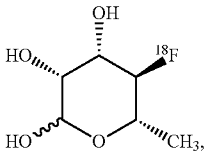,
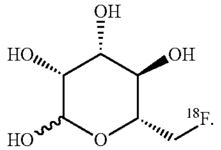.

ii) Radiolabeled Rhamnose Precursor

In other embodiments of Formula I, the compound is a precursor compound to a radiolabeled rhamnose analog. In such embodiments, each of $R^1$, $R^2$, $R^3$, and $R^4$ independently is $OR^6$ or $OR^7$, and $R^5$ is $OR^7$ or H, where at least one of $R^1$-$R^5$ is $OR^7$, and $R^6$ and $R^7$ are as previously defined. In some embodiments, exactly one of $R^1$-$R^5$ is $OR^7$, and the rest are $OR^6$.

The Rhamnose precursor compound may have a structure according to any one of Formulas III-a to III-e:

III-a

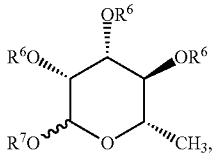,

III-b

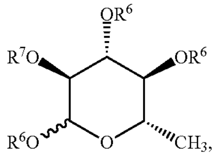,

III-c

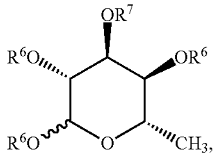,

-continued

III-d

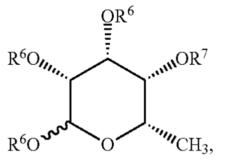

III-e

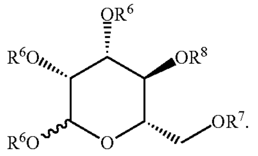

In an embodiment of Formulas I or III-a to III-e, $R^1$ is $OR^7$, $R^2$-$R^4$ are $OR^6$, and $R^5$ is H.

In an embodiment of Formulas I or III-a to III-e, $R^2$ is $OR^7$, $R^1$, $R^3$ and $R^4$ are $OR^6$, and $R^5$ is H.

In an embodiment of Formulas I or III-a to III-e, $R^3$ is $OR^7$, $R^1$, $R^2$ and $R^4$ are $OR^6$, and $R^5$ is H.

In an embodiment of Formulas I or III-a to III-e, $R^4$ is $OR^7$, $R^1$, $R^2$ and $R^3$ are $OR^6$, and $R^5$ is H.

In an embodiment of Formulas I or III-a to III-e, $R^5$ is $OR^7$, and $R^1$-$R^4$ are $OR^6$.

In some embodiments of Formulas I or III-a to III-e, $R^6$ is acetyl. In some embodiments, $R^7$ is triflate. And in certain embodiments, $R^6$ is acetyl and $R^7$ is triflate.

Exemplary Rhamnose analogs according to Formulas III-a to III-e include:

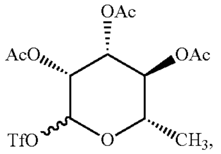

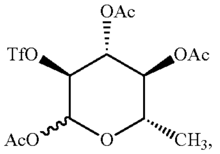

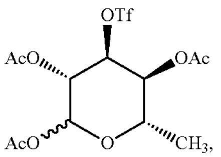

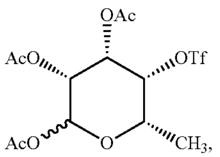

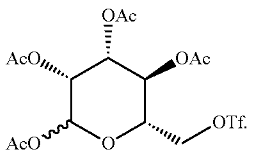

II. Cellobiose Analogs

In some embodiments of Formula I, the compound is a cellobiose analog. In such embodiments, $R^1$ is X, leading to compounds according to Formula IV:

Formula IV

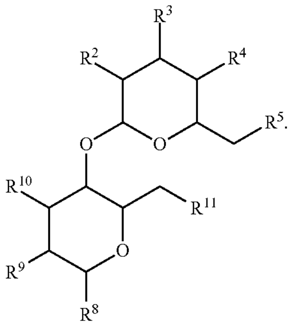

With respect to Formula IV, $R^2$-$R^{11}$ are as previously defined for Formula I, and condition (a) applies. In some embodiments, the cellobiose analog is a D-cellobiose analog.

i) Radiolabeled Cellobiose

In some embodiments of Formula IV, the cellobiose analog is a radiolabeled cellobiose analog, such as an $^{18}F$ radiolabeled cellobiose or deoxycellobiose analog. In some embodiments, each of $R^2$-$R^5$ and $R^8$-$R^{11}$ independently is $^{18}F$ or OH, where at least one of $R^2$-$R^5$ and $R^8$-$R^{11}$ is $^{18}F$. In some embodiments, one of $R^2$-$R^5$ and $R^8$-$R^{11}$ is $^{18}F$ and the rest of $R^2$-$R^5$ and $R^8$-$R^{11}$ are OH.

In some embodiments, the $^{18}F$ radiolabeled cellobiose or deoxycellobiose analog may have a Formula V Formula V

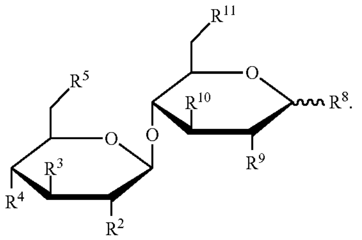

With respect to Formula IV, $R^2$-$R^5$ and $R^8$-$R^{11}$ are $^{18}F$ or OH, where at least one, and optionally exactly one of $R^2$-$R^5$ and $R^8$-$R^{11}$ is $^{18}F$.

In an embodiment of Formulas IV and V, $R^2$ is $^{18}F$ and $R^3$-$R^5$ and $R^8$-$R^{11}$ are OH.

In an embodiment of Formulas IV and V, $R^3$ is $^{18}F$ and $R^2$, $R^4$, $R^5$ and $R^8$-$R^{11}$ are OH.

In an embodiment of Formulas IV and V, $R^4$ is $^{18}F$ and $R^2$, $R^3$, $R^5$ and $R^8$-$R^{11}$ are OH.

In an embodiment of Formulas IV and V, $R^5$ is $^{18}F$ and $R^2$-$R^4$ and $R^8$-$R^{11}$ are OH.

In an embodiment of Formulas IV and V, $R^8$ is $^{18}F$ and $R^2$-$R^5$ and $R^9$-$R^{11}$ are OH.

In an embodiment of Formulas IV and V, $R^9$ is $^{18}F$ and $R^2$-$R^5$ and $R^8$, $R^{10}$ and $R^{11}$ are OH.

In an embodiment of Formulas IV and V, $R^{19}$ is $^{18}F$ and $R^2$-$R^5$ and $R^8$, $R^9$ and $R^{11}$ are OH.

In an embodiment of Formulas IV and V, $R^{11}$ is $^{18}F$ and $R^2$-$R^5$ and $R^8$-$R^{10}$ are OH.

In particular embodiments of Formulas IV and V, $R^9$ is $^{18}F$ and $R^2$-$R^5$ and $R^8$, $R^{10}$ and $R^{11}$ are OH, and in another particular embodiment of Formulas IV and V, $R^2$ is $^{18}F$ and $R^3$-$R^5$ and $R^8$-$R^{11}$ are OH.

Exemplary compounds according to Formulas IV and V include:

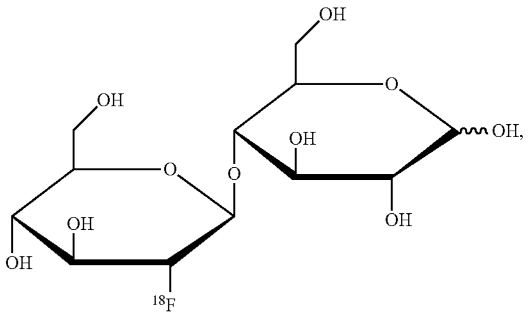

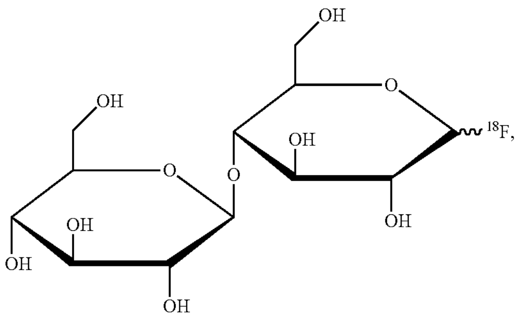

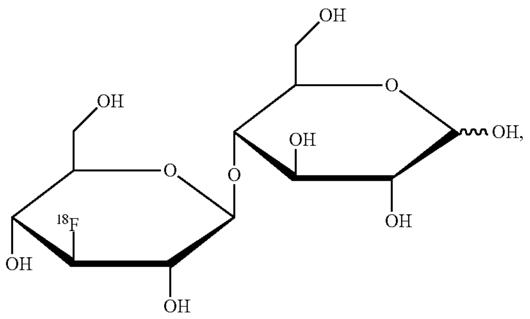

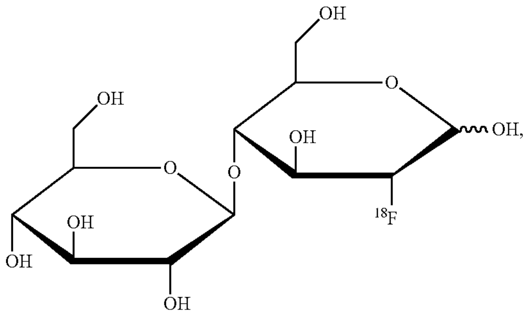

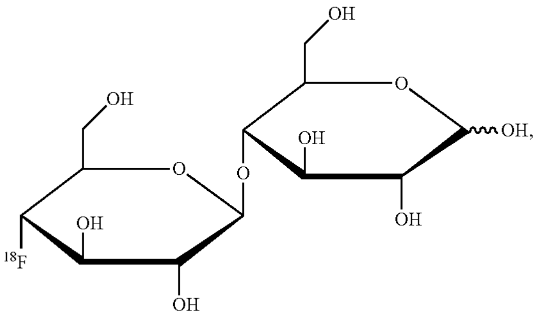

-continued

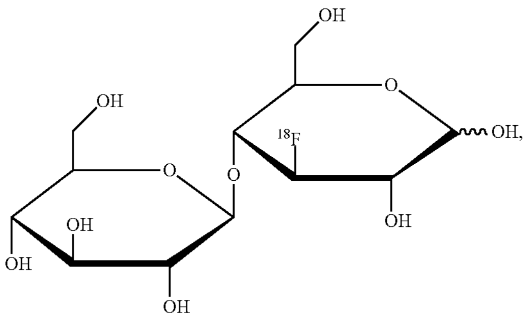

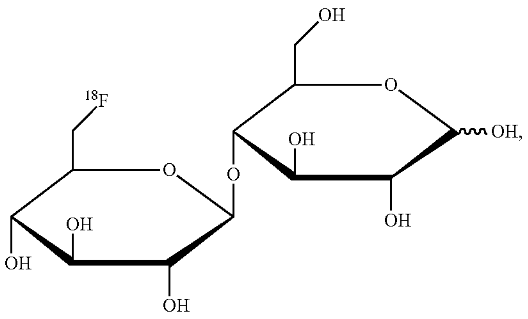

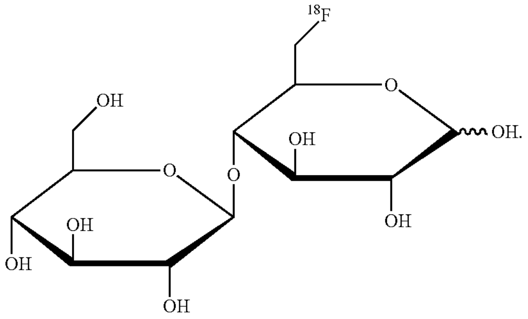

ii. Radiolabeled Cellobiose Precursor

In other embodiments of Formula IV, the compound is a precursor compound to a radiolabeled cellobiose analog. In such embodiments, each of $R^2$-$R^5$ and $R^8$-$R^{11}$ independently is $OR^6$ or $OR^7$, where at least one of $R^2$-$R^5$ and $R^8$-$R^{11}$ is $OR^7$. In some embodiments, one of $R^2$-$R^5$ and $R^8$-$R^{11}$ is $OR^7$ and the rest of $R^2$-$R^5$ and $R^8$-$R^{11}$ are $OR^6$.

The cellobiose precursor analog may have a structure according to any one of Formulas VI-a to VI-h:

VI-a

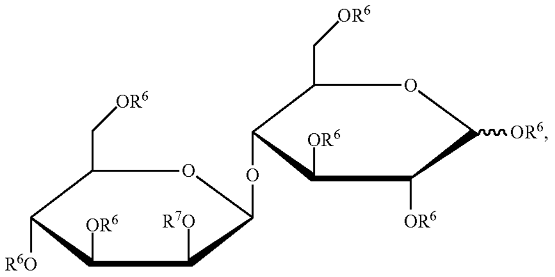

-continued

VI-b

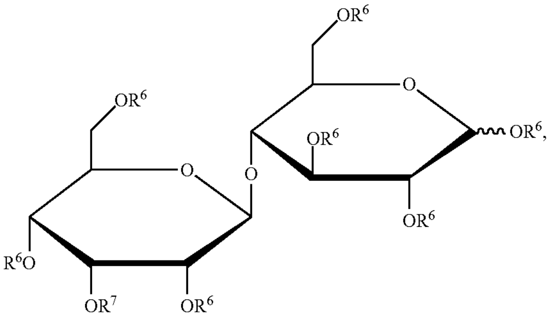

VI-c

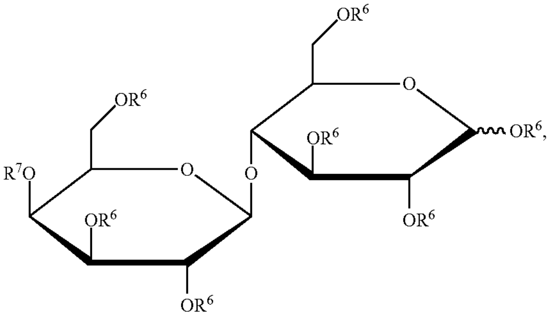

VI-d

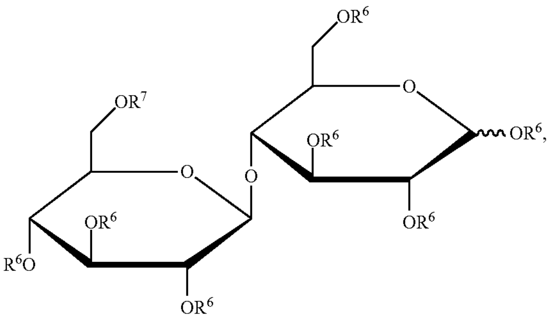

VI-e

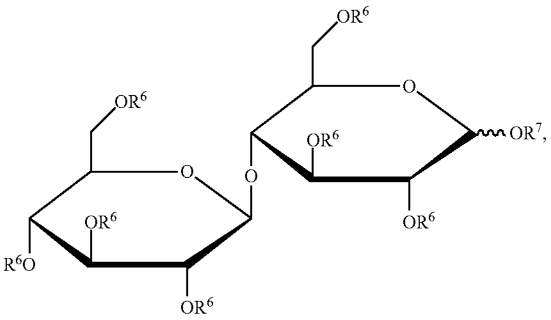

-continued

VI-f

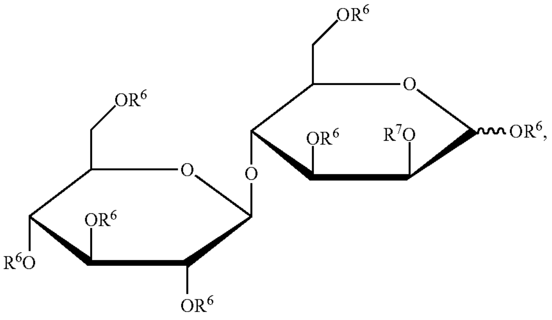

VI-g

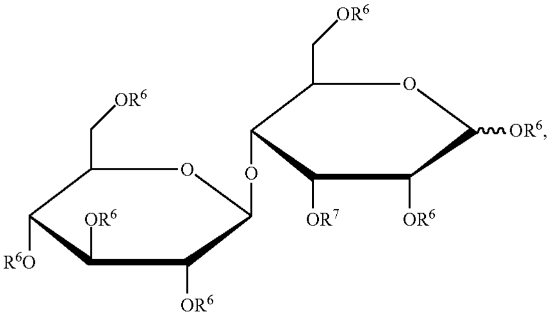

VI-h

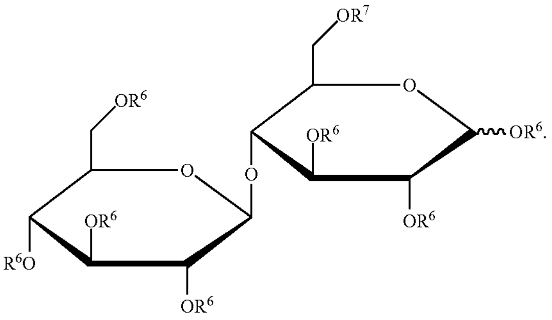

In an embodiment of Formulas IV and VI-a to VI-h, $R^2$ is $OR^7$ and $R^3$-$R^5$ and $R^8$-$R^{11}$ are $OR^6$.

In an embodiment of Formulas IV and VI-a to VI-h, $R^3$ is $OR^7$ and $R^2$, $R^4$, $R^5$ and $R^8$-$R^{11}$ are $OR^6$.

In an embodiment of Formulas IV and VI-a to VI-h, $R^4$ is $OR^7$ and $R^2$, $R^3$, $R^5$ and $R^8$-$R^{11}$ are $OR^6$.

In an embodiment, of Formulas IV and VI-a to VI-h $R^5$ is $OR^7$ and $R^2$-$R^4$ and $R^8$-$R^{11}$ are $OR^6$.

In an embodiment of Formulas IV and VI-a to VI-h, $R^8$ is $OR^7$ and $R^2$-$R^5$ and $R^9$-$R^{11}$ are $OR^6$.

In an embodiment of Formulas IV and VI-a to VI-h, $R^9$ is $OR^7$ and $R^2$-$R^5$ and $R^8$, $R^{10}$ and $R^{11}$ are $OR^6$.

In an embodiment, of Formulas IV and VI-a to VI-h $R^{10}$ is $OR^7$ and $R^2$-$R^5$ and $R^8$, $R^9$ and $R^{11}$ are $OR^6$.

In an embodiment of Formulas IV and VI-a to VI-h, $R^{H}$ is $OR^7$ and $R^2$-$R^5$ and $R^8$-$R^{10}$ are $OR^6$.

In particular embodiments of Formulas IV and VI-a to VI-h, $R^9$ is $OR^7$ and $R^2$-$R^5$ and $R^8$, $R^{10}$ and $R^{11}$ are $OR^6$, and in another particular embodiment, $R^2$ is $OR^7$ and $R^3$-$R^5$ and $R^8$-$R^{11}$ are $OR^6$.

In some embodiments of Formulas IV and VI-a to VI-h, $R^6$ is acetyl. In some embodiments, $R^7$ is triflate. And in certain embodiments, $R^6$ is acetyl and $R^7$ is triflate.

Exemplary compounds according to Formulas IV and VI-a to VI-h include:

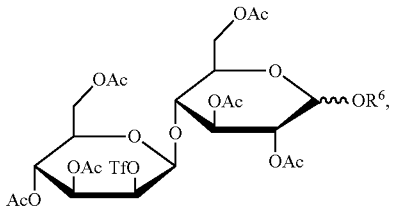

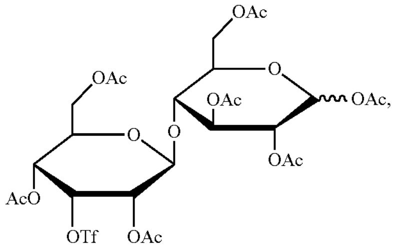

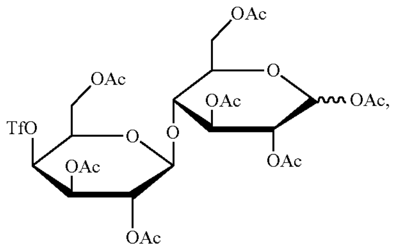

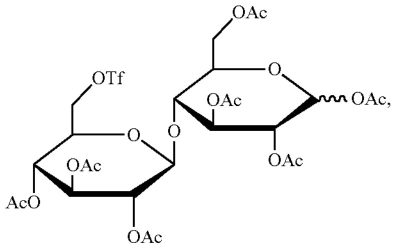

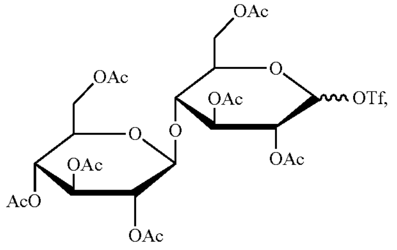

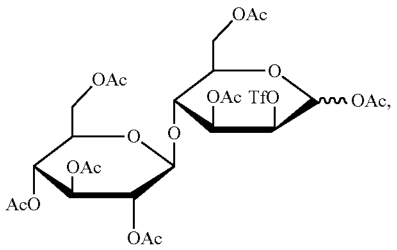

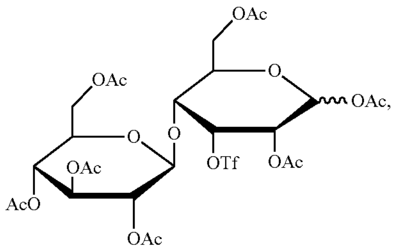

-continued

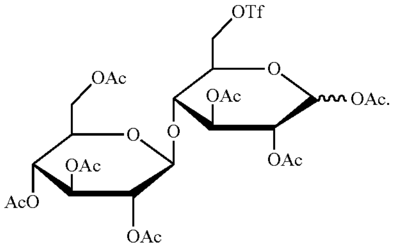

IV. Compositions

Also provided are compositions that include one or more of the radiolabeled compounds herein, such as an [$^{18}$F]-cellobiose or [$^{18}$F]-rhamnose compound. In some examples such a composition includes a pharmaceutically acceptable carrier, such as water or saline. Thus, in some examples the composition is a liquid composition, for example suitable for injection into a subject. In some examples the composition is frozen or freeze-dried. In some examples, the composition is present in a container, such as a glass or plastic vial.

V. Methods of Detecting Fungi

Provided here are in vivo and ex vivo/in vitro methods of using one or more of the radiolabeled compounds provided herein, such as [$^{18}$F]-cellobiose or [$^{18}$F]-rhamnose, to detect a fungus. The methods can detect any fungus of interest, such as an *Aspergillus, Candida, Cryptococcus*, or Mucormycetes. In some examples, the method detects *Aspergillus*, such as *A. fumigatus, A. flavus, A. terreus*, or *A. niger*. In some examples, the method detects *Candida*, such as *C. albicans*. In some examples, the method detects *Cryptococcus*, such as *C. neoformans* or *C. gattii*. In some examples, the method detects Mucormycetes, such as a *Rhizopus, Mucor, Rhizomucor, Syncephalastrum, Cunninghamella bertholletiae, Apophysomyces*, or *Lichtheimia*. The method can include contacting the fungus in vivo with one or more compounds or compositions provided herein, thereby detecting the fungus.

In some examples, the method is an in vivo method of detecting a fungal infection in a subject (such as any fungus provided above, or listed in Table 1 below; thus in some examples, the subject is one having a disease listed in Table 1). In some examples the subject is a mammal or bird or fish, such a human or veterinary subject. In some examples, the subject is immunocompromised, such as a cancer patient (e.g., one undergoing chemo and/or radiation therapy), a subject who has received a transplant (e.g., transplant of at least one of a stem cell or solid organ such as a lung, heart, liver, kidney, pancreas, or intestine), a subject having a primary immunodeficiency (examples of primary immunodeficiency diseases include those listed in Al-Herz et al. (Frontiers in Immunology, volume 5, article 162, Apr. 22, 2014, herein incorporated by reference in its entirety), e.g., T-B+ SCID, T-B− SCID, WHIM syndrome, IL-7 receptor severe combined immune deficiency (SCID), Adenosine deaminase deficiency (ADA) SCID, Purine nucleoside phosphorylase (PNP) deficiency, Wiskott-Aldrich syndrome (WAS), Chronic granulomatous disease (CGD), Leukocyte adhesion deficiency (LAD), Duchenne muscular dystrophy, Glycogen storage disease type IA, Retinal Dystrophy, and X-linked immunodeficiency with magnesium defect, Epstein-Barr virus infection, and neoplasia (XMEN)) or a subject with HIV. In such examples, the contacting includes administering one or more compounds or compositions provided herein (such as 1, 2, 3, 4 or 5 compositions) to a subject, and the method further includes subsequently performing diagnostic imaging (such as nuclear imaging) of the subject, thereby detecting the fungal infection in the subject. For example, the diagnostic imaging can be performed at least 15 minutes, at least 20 minutes, at least 30 minutes, at least 45 minutes, at least 60 minutes, or at least 120 minutes, such as 15 to 30, 15 to 60, 30 to 60, 30 to 120, or 60 to 120 minutes after administering the one or more compounds to the subject. In some examples, administering includes injection into the subject, such as IV administration. In some examples, depending on the size and weight of the subject, a least 1 millicurie, at least 2 millicuries, at least 3 millicuries, at least 4 millicuries, at least 5 millicuries, at least 10 millicuries, such as 1-3, 1-5, 1-10, 1-20, 5-20 or 5-10 millicuries of the one or more compounds is administered to the subject.

In some examples, diagnostic imaging of the subject includes nuclear imaging of the brain, lungs, heart, sinuses, and/or abdomen of the subject. In some examples, positron emission tomography (PET) nuclear imaging technology is used. PET enables visualization of metabolic processes in vivo. PET imaging detects pairs of gamma rays emitted indirectly by a positron-emitting radionuclide (such as $^{18}$F in [$^{18}$F]-cellobiose or [$^{18}$F]-rhamnose). PET systems have sensitive detector panels to capture gamma ray emissions from inside the body and use software to plot and triangulate the source of the emissions, creating 3-D computed tomography images of the tracer concentrations within the body.

The in vivo methods can be used to detect a fungal infection in a subject. such as in the blood, kidney, heart, esophagus, lungs, sinuses, gastrointestinal tract, and/or central nervous system (e.g., brain, spinal cord). Detection of the administered radiolabeled compound(s) provided herein, such as [$^{18}$F]-cellobiose or [$^{18}$F]-rhamnose, indicates the presence (and location) of a fungal infection. In some examples, such methods are used to monitor treatment of a fungal infection. Thus, in some examples, the subject is one who has previously been treated with one or more anti-fungal compositions.

Also provided are ex vivo or in vitro methods of detecting a fungus, for example by incubating or contacting the one or more radiolabeled compounds with a sample containing the fungus, for example a biological sample obtained from a subject, thereby detecting the fungal infection. The method can further include detecting the uptake of the radiolabeled compound(s) provided herein, such as [$^{18}$F]-cellobiose or [$^{18}$F]-rhamnose, in the sample, for example by using a beta counter, radioTLC or autoradiography.

VI. Methods of Treatment

Also provided are methods of treating a subject diagnosed with fungal infection using the methods provided herein. In some examples, treatment includes administering to the subject a therapeutically effective amount of one or more anti-fungal compounds. Any conventional methods of administration can be used, such as injection, inhalation, and oral administration. Exemplary anti-fungal compounds that can be administered include therapeutically effective amounts of one or more of itraconazole, a corticosteroid, voriconazole, amphotericin B, posaconazole, isavuconazole, caspofungin, micafungin, clotrimazole, miconazole, nystatin, fluconazole, anidulafungin and flucytosine.

Exemplary diseases and treatments are provided in Table 1.

TABLE 1

Fungal diseases affecting patients with weakened immune system

| Fungus | Disease manifestations | Method of treatment |
| --- | --- | --- |
| Aspergillosis | Most common is *Aspergillus fumigatus*; can be very aggressive especially in immunocompromised patients with high mortality and morbidity. Manifestations include lung disease (invasive pulmonary aspergillosis) and hematogenous spread with potential CNS involvement (cerebral aspergillosis). Both are associated with very high mortality | Allergic aspergillosis: Itraconazole +/− corticosteroids Invasive aspergillosis: Voriconazole + Other options: lipid amphotericin B formulations, posaconazole, isavuconazole, itraconazole, caspofungin, and micafungin |
| Mucormycosis | *Rhizopus*, *Mucor* or *Rhizomucor* species. Most commonly affects the sinuses or the lungs after inhaling fungal spores from the air, or the skin after the fungus enters the skin through a cut, burn, or other type of skin injury. | Amphotericin B, posaconazole, or isavuconazole |
| Candidiasis | Most common is *Candida albicans*. The most serious is invasive candidiasis whichoccurs when *Candida* species enter the bloodstream or affect internal organs like the kidney, heart, or brain. | Mucosal → clotrimazole, miconazole, or nystatin. For severe infections → fluconazole Invasive: echinocandin (caspofungin, micafungin, or anidulafungin) given IV. Fluconazole, amphotericin B may also be appropriate in certain situations. |
| Cryptococcosis | Most common is *Cryptococcus neoformans*. Brain infections due to *Cryptococcus* are called cryptococcal meningitis. Most cases occur in immunocompromised patients, particularly those who have advanced HIV/AIDS, but can also occur in seemingly immunocompetent subjects. | Mild-to-moderate pulmonary infections → fluconazole. Severe lung infections or CNS infections → amphotericin B in combination with flucytosine, followed by long course of fluconazole |

VII. EXAMPLES

Example 1

Synthesis of 2-deoxy-2-fluororhamnose

(3R,4R,5S,6S)-6-methyltetrahydro-2H-pyran-2,3,4,5-tetrayl Tetraacetate

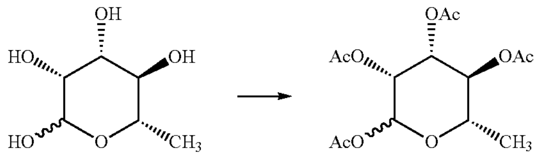

1 2

Compound 2 was prepared according to the method described by Toyokuni et al., *Mol Imaging Biol.* 2004, 6(5):324-330. Briefly, L-Rhamnose (10 g, 54.9 mmol) was carefully added in portions (3 portions in 15 minutes) to a stirring solution of iodine (0.125 g, 0.49 mmol) in acetic anhydride (60 mL) under a cool water bath (10-15° C.). The resulting mixture was allowed to warm up to room temperature and stirred for 2 hours. The mixture was then poured on a mixture of crushed ice and saturated aqueous $Na_2S_2O_3$ (250 mL, 1:1 mixture) with vigorous stirring. To the resulting light yellow mixture under ice-water bath, $NaHCO_3$ was added portion wise until no more $CO_2$ was released. The crude product was extracted with $CH_2Cl_2$ (150 mL×3). The organic layer was combined, washed with saturated $NaHCO_3$ solution and water (400 mL each), and dried over anhydrous $Na_2SO_4$. Crude product 2 was obtained by removing the volatiles under reduced pressure (19.33 g, 95.4% yield, α:β anomer ratio=3:1).

$^1H$ NMR (400 MHz, Chloroform-d) δ 6.02 (d, J=1.9 Hz, 1H), 5.83 (s, 0.34H), 5.48 (s, 0.34H), 5.36-5.28 (m, 1H), 5.26 (dd, J=3.5, 2.0 Hz, 1H), 5.18-5.05 (m, 1.7H), 4.00-3.90 (m, 1H), 3.72-3.62 (m, 0.36H), 2.23 (s, 4H), 2.22, (s, 1H), 2.20 (s, 3H), 2.15 (s, 3H), 2.11 (s, 1H), 2.07 (s, 4H), 2.01 (s, 4H), 1.30 (d, J=6.2 Hz, 1H), 1.25 (d, J=6.2 Hz, 3H). MS (ESI) calculated mass for the parent $C_{14}H_{20}O_9$ 332.11 [M]. found 355.00 [M+Na].

(5S,6S,7R,7aR)-2-ethoxy-2,5-dimethyltetrahydro-5H-[1,3]dioxolo[4,5-b]pyran-6,7-diyl Diacetate

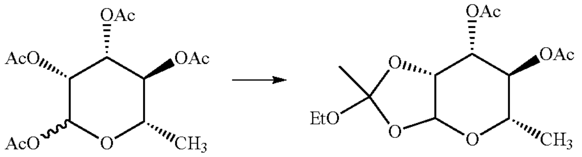

2 3

To a solution of Compound 2 (19.33 g, 58.2 mmol) in glacial acetic acid (20 mL) and acetic anhydride (1.6 mL) was added HBr in acetic acid (30%, 20 mL) dropwise under ice water bath and vigorous stirring. The resulting mixture was stirred under room temperature overnight and slowly quenched with pre-cooled saturated $NaHCO_3$ solution (500 mL). The brominated intermediate was extracted with $CHCl_3$ (200 mL×2). The organic layer was combined, dried over anhydrous $Na_2SO_4$. The bromide intermediate was obtained by removing the volatiles under reduced pressure as a yellow oil (17.8 g).

The oily bromide intermediate was dissolved in a mixture of anhydrous acetonitrile (8 mL), and 2,4,6-collidine (11 mL), ethanol (200 proof, 13 mL) was added. The resulting mixture was stirred under room temperature overnight, diluted with $CH_2Cl_2$ (300 mL) and washed water (300 mL×2) and brine (200 mL). The organic layer was dried over anhydrous $Na_2SO_4$. Crude product was obtained by removing the volatiles under reduced pressure. Product 3 was purified by flash column chromatography with hexane/ethyl acetate 4/1 to 2/1 gradient (7.8 g, 42.2% yield for 2 steps).

$^1H$ NMR (400 MHz, Chloroform-d) δ 5.41 (d, J=2.4 Hz, 1H), 5.16-5.02 (m, 2H), 4.59 (dd, J=3.8, 2.4 Hz, 1H), 3.65-3.47 (m, 3H), 2.12 (s, 3H), 2.07 (s, 3H), 1.75 (s, 3H), 1.30-1.14 (m, 6H). MS (ESI) calculated mass for the parent $Cl_4H_{22}O_8$ 318.13 [M]. found 341.00 [M+Na].

(3R,4S,5S,6S)-3-hydroxy-6-methyltetrahydro-2H-pyran-2,4,5-triyl Triacetate

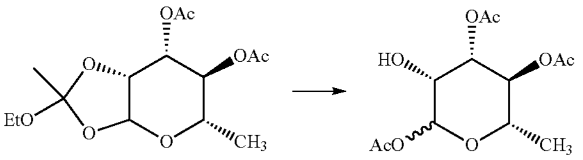

3 4

Hydrochloric acid (1N, 10 mL) was added to a solution of the orthoester 3 (7 g, 22.0 mmol) and acetone (15 mL). The mixture was stirred under room temperature for 10 minutes and volatiles were removed under reduced pressure. The resulting crude product was dissolved in $CH_2Cl_2$ (150 mL) and washed with water (150 mL×2). The organic layer was dried over anhydrous $Na_2SO_4$. Crude product was obtained by removing the volatiles under reduced pressure. Product 4 was purified by flash column chromatography with hexane/ethyl acetate 4/1 to 1/1 gradient (3.15 g, 49.3% yield).

$^1H$ NMR (400 MHz, Chloroform-d) δ 5.76 (s, 1H), 5.15 (t, J=9.8 Hz, 1H), 4.99 (dd, J=9.9, 3.0 Hz, 1H), 4.22-4.15 (m, 1H), 3.65 (dq, J=9.3, 6.2 Hz, 1H), 2.5-2.25 (br s, 1H), 2.17 (s, 3H), 2.11 (s, 3H), 2.06 (s, 3H), 1.27 (d, J=6.2 Hz, 3H). MS (ESI) calculated mass for the parent $C_{12}H_{18}O_8$ 290.10 [M]. found 313.00 [M+Na].

(3S,4S,5S,6S)-3-hydroxy-6-methyltetrahydro-2H-pyran-2,4,5-triyl Triacetate

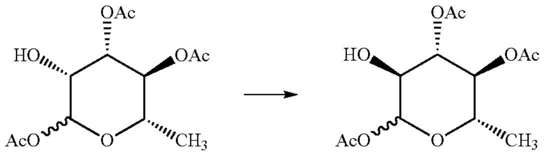

4 5

The triacetate 4 (1.0 g, 3.19 mmol) was dissolved in anhydrous $CH_2Cl_2$ (20 mL) and anhydrous pyridine (3.5 mL) and cooled with ice-salt bath. Trifluoromethanesulfonic anhydride (4.5 g, 15.97 mmol) in $CH_2Cl_2$ (10 mL) was added dropwise. The mixture was stirred under room temperature for 20 minutes, sequentially washed with HCl (0.3 M, 30 mL), saturated $NaHCO_3$ (30 mL) and brine (30 mL). The organic layer was dried over anhydrous $Na_2SO_4$. The crude triflate was obtained by removing the volatiles under reduced pressure.

The crude triflate (1.35 g) was stirred with acetonitrile (30 mL) and tetrabutylammonium nitrate (4.59 g, 16.0 mmol) under room temperature for 1 hour. Crude product was obtained by removing the volatiles under reduced pressure. Product 5 was purified by flash column chromatography with hexane/ethyl acetate 3/1 to 1/1 gradient (0.65 g, 65% yield for 2 steps).

$^1H$ NMR (400 MHz, Chloroform-d) δ 5.58 (d, J=8.3 Hz, 1H), 5.07 (t, J=9.5 Hz, 1H), 4.77 (t, J=9.6 Hz, 1H), 3.76-3.60 (m, 2H), 3.05 (s, 1H), 2.15 (s, 3H), 2.07 (s, 5H), 2.04 (s, 4H), 1.20 (d, J=6.2 Hz, 3H). MS (ESI) calculated mass for the parent $C_{12}H_{18}O_8$ 290.10 [M]. found 313.00 [M+Na].

(3S,4R,5S,6S)-6-methyl-3-(((trifluoromethyl)sulfonyl)oxy)tetrahydro-2H-pyran-2,4,5-triyl Triacetate

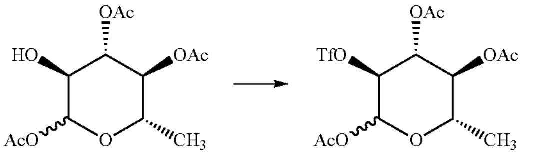

5 6

The triacetate 5 (0.52 g, 1.79 mmol) was dissolved in anhydrous $CH_2Cl_2$ (20 mL) and anhydrous pyridine (1.2 mL) and cooled with ice-salt bath. Trifluoromethanesulfonic anhydride (1.52 g, 5.37 mmol) in $CH_2Cl_2$ (10 mL) was added dropwise. The mixture was stirred under room temperature for 20 minutes, sequentially washed with HCl (0.3 M, 30 mL), saturated $NaHCO_3$ (30 mL) and brine (30 mL). The organic layer was dried over anhydrous $Na_2SO_4$. Crude product was obtained by removing the volatiles under reduced pressure. Flash column chromatography was used to purify the product 6 with hexane/ethyl acetate 3/1 to 1/1 gradient (0.75 g, quant. yield).

$^1H$ NMR (400 MHz, Chloroform-d) δ 5.80 (d, J=8.3 Hz, 1H), 5.38 (t, J=9.6 Hz, 1H), 4.89-4.76 (m, 2H), 3.78 (dq, J=9.7, 6.1 Hz, 1H), 2.16 (s, 3H), 2.07 (s, 3H), 2.05 (s, 3H), 1.25 (d, J=6.2 Hz, 3H). $^{13}C$ NMR (101 MHz, $CDCl_3$) δ 169.53, 169.51, 168.44, 118.21 (q, J=319.0 Hz), 90.21, 80.92, 77.35, 77.23, 77.03, 76.71, 73.02, 71.27, 71.24, 20.49, 20.37, 20.26, 17.02. MS (ESI) calculated mass for the parent $C_{13}H_{17}F_3O_{10}S$ 422.05 [M]. found 362.90 [M-OAc].

(3R,4R,5S,6S)-3-fluoro-6-methyltetrahydro-2H-pyran-2,4,5-triol Triacetate

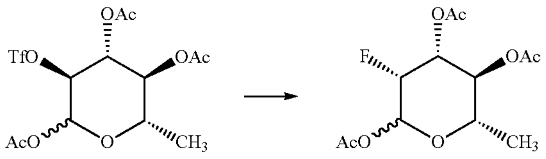

6 7

To a solution of triflate 6 (50 mg, 0.118 mmol) in anhydrous acetonitrile (2 mL) was added TBAF in THF (1.0 M, 0.177 mL, 0.177 mmol). The solution was stirred under 65° C. overnight. The volatiles were removed under reduced pressure. Flash column chromatography was used to purify the product 7 with hexane/ethyl acetate 5/1 to 2/1 gradient (3.5 mg, 10% yield, α: β anomer ratio=1:1). The product characterization was identical with the literature.

$^1H$ NMR (400 MHz, Chloroform-d) δ 6.02 (s, 1H), 5.78 (d, J=60 Hz, 1H), 5.35-5.30 (m, 1H), 3.30-5.25 (m, 1H), 5.18-5.10 (m, 2H), 5.08-4.95 (m, 1H), 4.88 (dd, J=120, 4.0 Hz, 1H), 4.00-3.80 (m, 1H), 3.73-3.65 (m, 1H), 2.20 (s, 3H), 2.09 (s, 3H), 2.08 (s, 3H), 2.12 (s, 3H), 2.08 (s, 3H), 2.02 (s, 3H), 1.30 (d, J=6.0 Hz, 3H), 1.25 (d, J=6.0 Hz, 3H). MS (ESI) calculated mass for the parent $C_{12}H_{17}FO_7$ 292.10 [M]. found 273.10 [M-F].

(3R,4R,5R,6S)-3-fluoro-6-methyltetrahydro-2H-pyran-2,4,5-triol (2-deoxy-2-fluororhamnose)

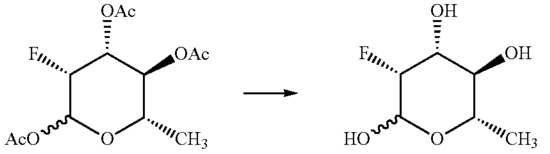

7 8

2-deoxy-2-fluorohamnose

Triacetate 7 (3.5 mg, 0.012 mmol) was dissolved in TFA (1.0 mL) and stirred under 50° C. for 1 hour. The volatiles were removed under reduced pressure to yield 2-deoxy-2-fluororhamnose as a yellow oil (1.2 mg). $^{19}F$ NMR chromatogram was compared with literature which found identical result. (Liu et al., *Chem. Eur. J.* 2016, 22, 12557-12565.)

Example 2

Radiosynthesis of 2-deoxy-2-[$^{18}F$]fluororhamnose

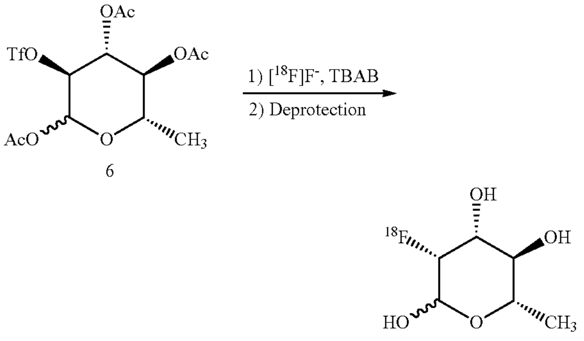

6

9

Radiosynthesis of 2-deoxy-2-[$^{18}F$]fluororhamnose was performed on a GE Tracerlab FX-N2 synthesizer. The synthesis comprised 9 reagent vials on the GE synthesizer. Vials 1-5 were used for the elution, drying of F-18, and fluorination reaction. Vials 13-14 were used for the formulation of purified intermediate, and vials 9-10 for the hydrolysis and formulation of final product [$^{18}$F]. Specifically, Vial 1 was added with tetrabutylammonium bicarbonate solution (150 μL, 0.075M), 50 μL water and MeOH (1 mL); Vial 2 was added with acetonitrile (ACN) (1 mL); Vial 3 was added with the tosylate precursor 2 (5 mg) in ACN (0.6 mL); Vial 4 was added with water (0.5 mL); Vial 4 was added with 1 mL water; Vial 5 was added with HPLC solvent (2.0 mL, 40% ACN in 0.1% trifluoroacetic acid (TFA)); Vial 9 was added with HCl (1N, 700 μL); Vial 10 was added with NaOH (1N, 500 μL); Vial 13 was added with EtOH (1.2 mL); Vial 14 was added with water (6 mL); HPLC dilution flask was added with water (30 mL). Vial 11 inlet port was connected with valve 15 (V15) right port for transferring intermediate to reaction vial 2 (RV2).

Typically, 7.4 GBq (200 mCi) [$^{18}$F]fluoride in 2.5 mL of water was passed through a PS—$HCO_3$ cartridge, which was rinsed with 1 mL of acetonitrile. [$^{18}$F]fluoride was eluted from the cartridge into reactor 1 (R1) with the eluent in Vial 1, and dried under $N_2$/vacuum at 75° C. for 4 minutes. R1 was cooled to 50° C., acetonitrile in Vial 2 was added and the activity was azeotropically dried at 55° C. for 3 minutes and at 95° C. for 3 minutes under $N_2$/vacuum. The activity was further dried using a vacuum for 3 minutes. The [$^{18}$F]fluoride drying cycle took about 20 minutes.

The tosylate precursor solution in Vial 3 was added to the dried activity. The resulting solution was stirred at 70° C. for 20 minutes, then cooled to 45° C. The reaction mixture was diluted with 1.0 mL of water (Vial 4), and transferred in Tube 2. R1 was rinsed with HPLC mobile phase (Vial 5) and the solution was also transferred to Tube 2. The solution in Tube 2 was thoroughly mixed by bubbling $N_2$ for 10 seconds and injected into the HPLC for purification. HPLC condition: Phenomenex Luna (2) C18 column, 250×10 mm, 5 μm. Mobile phase: 40% ACN in 0.1% TFA. Flow rate: 4 mL/min. The labeled intermediate was eluted at about 12-14 minutes. The intermediate was collected in the dilution flask containing 30 mL water, and passed through an Oasis HLB plus cartridge (pre-conditioned with 5 mL of ethanol, 10 mL of air, and 10 mL of water). The trapped intermediate was rinsed with 6 mL water (Vial 14), and eluted with 1.2 mL of absolute ethanol (Vial 13) to R2 through value 35 (V35).

The eluted intermediate was heated to 60° C. under $N_2$ flow and vacuum for 3 minutes to remove ethanol. NaOH in Vial 10 was added to the dried residue. The resulting solution was heated at 45° C. for 10 minutes. HCl solution in Vial 9 was added, the content was transferred through V16 and an in-line sterile filter to the product vial. The product was analyzed by HPLC. HPLC conditions: Waters BEH Amide column (150*4.6 mm), 3.5 μm. Using 90%-50% D in 8 minutes. C: 95% water+5% ACN with 0.1% $NH_4OH$; D: 95% ACN+5% water with 0.1% $NH_4OH$. The product peak eluted at about 4 minutes. Generally, 2-deoxy-2-[$^{18}$F]fluororhamnose 9 was synthesized in 7-12% radiochemical yield (uncorrected, n>5), radiochemical purity >95%. The synthesis time was about 90 minutes.

A manual method also was used to produce the radiolabeled product. Different bases were tried and produced various overall yields.

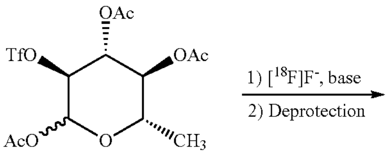

-continued

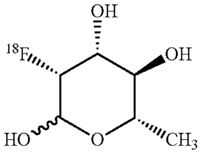

2-[$^{18}$F]deoxy-2-fluoro-L-rhamnose

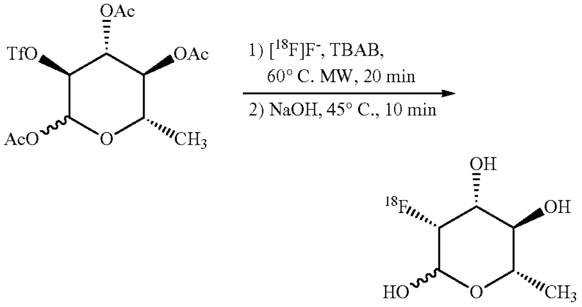

2-[$^{18}$F]deoxy-2-fluoro-L-rhamnose

| Precursor (mg) | Base | Temp. (° C.) | Time (min) | RCY (%) |
|---|---|---|---|---|
| 3 | $K_2CO_3$ (2 mg) | 100 | 10 | n/a |
| 3 | $K_2CO_3$ (2 mg) | 60 | 20 | n/a |
| 3 | TBAB (100 μL, 0.075M) | 60 | 20 | 10-34 |
| 3 | TBAB (100 μL, 0.075M) | 45 | 20 | 20-50 |
| 3 | TBAB (100 μL, 0.075M) | rt | 20 | 5% |
| 5 | "Rxn on Sep-pak" method | | | n/a |

Example 3

Synthesis of 6-F-Rhamnose

(3S,5S,6R)-6-((trityloxy)methyl)tetrahydro-2H-pyran-2,3,4,5-tetrayl Tetraacetate

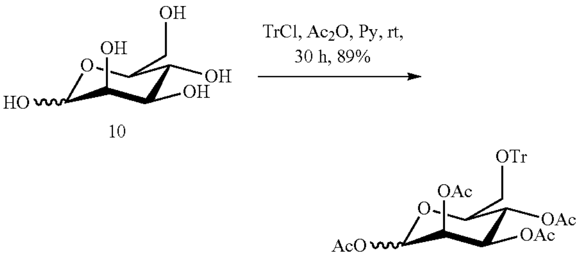

10

11

Triphenylmethyl chloride (3.4 g, 12.2 mmol) was added to L-Mannose 10 (2.00 g, 11.1 mmol) in anhydrous pyridine (10 mL). The mixture was stirred at room temperature for 15 hours. 6 mL of $Ac_2O$ was added afterwards and the solution was stirred for another 15 hours. The mixture was poured into ice-cold water and extracted with EtOAc (3×100 mL). The combined organic layer was washed with brine and dried over $Na_2SO_4$. After evaporation of solvents, the residue was purified by silica gel flash chromatography to afford the product 11 as a white solid (5.84 g, 89%).

$^1H$ NMR (400 MHz, $CDCl_3$): δ 7.46-7.22 (m, 15H), 6.10 (s, 0.7H), 5.85 (s, 0.3H), 5.52 (m, 1H), 5.43-5.52 (m, 2H), 3.91 (m, 0.7H), 3.64 (m, 0.3H), 3.34 (m, 1H), 3.18 (0.3H), 3.07 (m, 0.7H), 2.24 (s, 2.1H), 2.23 (s, 0.9H), 2.17 (s, 2.1H), 2.14 (s, 0.9H), 2.00 (s, 2.1H), 1.98 (s, 0.9H), 1.76 (s, 0.9H), 1.75 (s, 2.1H).

(3S,5S,6R)-6-(hydroxymethyl)tetrahydro-2H-pyran-2,3,4,5-tetrayl Tetraacetate

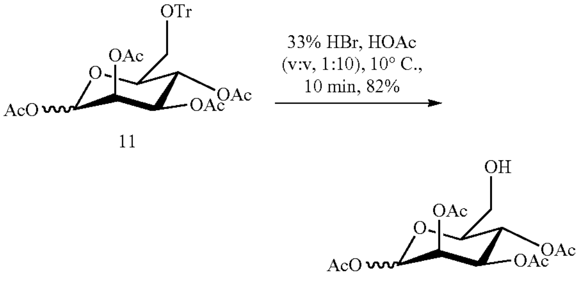

11
12

33% HBr in HOAc (1.6 mL) was added to the solution of compound 11 (4.60 g, 7.80 mmol) in glacial acetic acid (16 mL) at 10° C. The mixture was stirred for 10 minutes. The formed triphenylmethyl bromide was immediately removed by filtration. The filtrate was diluted with cold water and extracted with EtOAc (3×100 mL). The combined organic layer was washed with water, brine and dried over $Na_2SO_4$. After evaporation of solvents, the residue was purified by silica gel flash chromatography to afford the product 12 as a white solid (2.23 g, 82%).

$^1H$ NMR (400 MHz, $CDCl_3$): δ 6.09 (d, 0.67H, J=1.6 Hz), 5.87 (d, 0.33H, J=1.2 Hz), 5.49 (dd, 0.33H, J=1.2 and 11.5 Hz), 5.40 (dd, 0.67H, J=3.3 and 10.0 Hz), 5.33 (m, 0.67H), 5.27 (m, 1H), 5.17 (dd, 0.33H, J=3.3 and 10.5 Hz), 3.85 (m, 0.67H), 3.73 (m, 1H), 3.66-3.58 (m, 1.33H), 2.21 (s, 0.99H), 2.17 (s, 2.01H), 2.16 (s, 2.01H), 2.10 (s, 0.99H), 2.08 (s, 2.01H), 2.04 (s, 0.99H), 2.02 (s, 2.01H), 2.01 (s, 0.99H).

3S,5S,6R)-6-((((trifluoromethyl)sulfonyl)oxy)methyl)tetrahydro-2H-pyran-2,3,4,5-tetrayl Tetraacetate

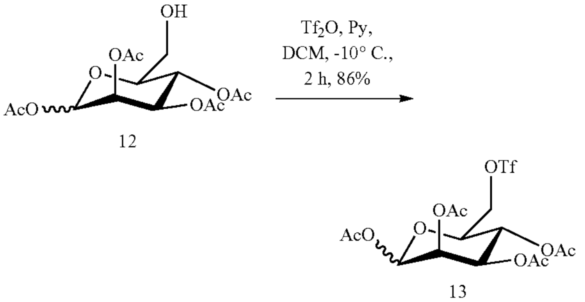

12
13

Trifluoromethanesulfonic anhydride (0.37 mL, 2.2 mmol) was added to a mixture of compound 12 (696 mg, 2.0 mmol) and pyridine (0.25 mL) in dichloromethane (20 mL) at −10° C. After stirring for 2 hours, water (50 mL) was added. The organic layer was separated and the aqueous layer was extracted with dichloromethane (3×50 mL). The organic layers were combined, washed with 10% $H_2SO_4$, sat. $NaHCO_3$, brine and dried over $MgSO_4$. After evaporation of solvents, the residue was purified by silica gel flash chromatography to afford the product 13 as a white solid (826 mg, 86%).

$^1H$ NMR (400 MHz, $CDCl_3$): δ 6.12 (d, 0.62H, J=2.0 Hz), 5.89 (d, 0.38H, J=1.2 Hz), 5.49 (dd, 0.38H, J=1.2 and 3.1 Hz), 5.39 (dd, 0.62H, J=3.1 and 10.2 Hz), 5.33 (m, 0.62H), 5.30 (m, 0.38H), 5.26 (dd, 0.62H, J=1.2 and 11.5 Hz), 5.16 (dd, 0.38H, J=3.1 and 9.8 Hz), 4.58-4.54 (m, 2H), 4.14 (m, 0.62H), 3.92 (m, 0.38), 2.22 (s, 1.14H), 2.19 (s, 1.86H×2), 2.12 (s, 1.14H), 2.10 (s, 1.86H), 2.05 (s, 1.14H), 2.03 (s, 1.86H), 2.02 (s, 1.14H). $^{19}F$ NMR (376 MHz, $CDCl_3$): δ −74.3, −74.4.

(3S,4R,5R,6R)-6-(fluoromethyl)tetrahydro-2H-pyran-2,3,4,5-tetrayl Tetraacetate

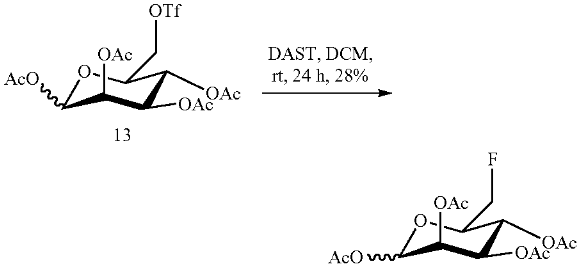

13
14

DAST (0.30 mL, 2.27 mmol) was slowly added to a solution of 13 (104 mg, 0.30 mmol) in anhydrous $CH_2Cl_2$ (5 mL) at −40° C. The reaction was stirred at room temperature for 24 hours. After cooled down to −20° C., MeOH (1 mL) was added and the solvent was removed under reduced pressure. The residue was diluted with $CH_2Cl_2$ (75 mL), washed with water and dried over $MgSO_4$. After evaporation of solvents, the residue was purified by silica gel flash chromatography to afford the product 14 as a colorless oil (30 mg, 28%). $^{19}F$ NMR (376 MHz, $CDCl_3$): δ −231.9, −232.4.

(3S,4R,5R,6R)-6-(fluoromethyl)tetrahydro-2H-pyran-2,3,4,5-tetraol

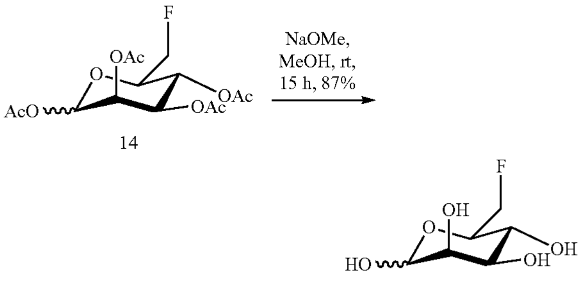

14
15

NaOMe (13.5 mg, 0.25 mmol) was added to a suspension of 14 (22 mg, 0.063 mmol) in dry MeOH (3 mL). The mixture was stirred at room temperature for 15 hours. Then the reaction mixture was neutralized with Dowex (H+) resin, filtrated, concentrated and purified by silica gel flash column chromatography to afford 15 as a white solid (10 mg, 87%).

$^1$H NMR (400 MHz, $D_2O/CD_3OD$): δ 5.18 (d, 0.6H, J=2.0 Hz), 4.92 (d, 0.4H, J=1.2 Hz), 4.78-4.57 (m, 2H), 3.93 (m, 1H), 3.87 (m, 1H), 3.77 (m, 1H), 3.68 (m, 1H).

Example 4

Radiosynthesis of 6-[$^{18}$F]fluororhamnose

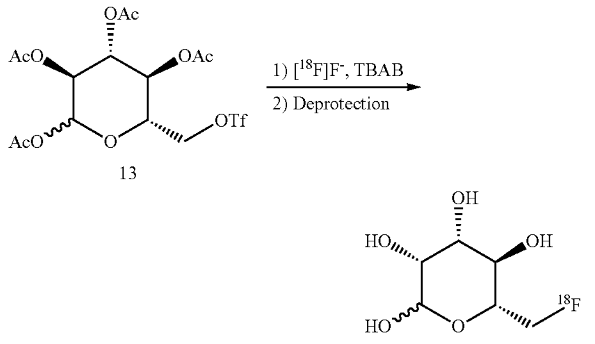

13

16

Radiosynthesis of 6-[$^{18}$F]fluororhamnose was performed on a GE Tracerlab FX-N2 synthesizer. The synthesis comprised 9 reagent vials on the GE synthesizer. Vials 1-5 were used for the elution, drying of F-18, and fluorination reaction. Vials 13-14 were used for the formulation of purified intermediate, and vials 9-10 for the hydrolysis and formulation of final product [$^{18}$F]16. Specifically, Vial 1 was added with tetrabutylammonium bicarbonate solution (150 μL, 0.075M), 50 μL water and MeOH (1 mL); Vial 2 was added with ACN (1 mL); Vial 3 was added with the tosylate precursor 2 (5 mg) in ACN (0.6 mL); Vial 4 was added with water (0.5 mL); Vial 4 was added with 1 mL water; Vial 5 was added with HPLC solvent (2.0 mL, 40% ACN in 0.1% TFA); Vial 9 was added with HCl (1N, 700 μL); Vial 10 was added with NaOH (1N, 500 μL); Vial 13 was added with EtOH (1.0 mL); Vial 14 was added with water (6 mL); HPLC dilution flask was added with water (30 mL). Vial 11 inlet port was connected with V15 right port for transferring intermediate to RV2.

Typically, 7.4 GBq (200 mCi) [$^{18}$F]fluoride in 2.5 mL of water was passed through a PS—$HCO_3$ cartridge, which was rinsed with 1 mL of acetonitrile. [$^{18}$F]fluoride was eluted from the cartridge into reactor 1 (R1) with the eluent in Vial 1, and dried under $N_2$/vacuum at 75° C. for 4 minutes. R1 was cooled to 50° C., acetonitrile in Vial 2 was added and the activity was azeotropically dried at 55° C. for 3 minutes and at 95° C. for 3 minutes under $N_2$/vacuum. The activity was further dried using a vacuum for 3 minutes. The [$^{18}$F]fluoride drying cycle took about 20 minutes.

The tosylate precursor solution in Vial 3 was added to the dried activity. The resulting solution was stirred at 70° C. for 20 minutes, cooled to 45° C. The reaction mixture was diluted with 1.0 mL of water (Vial 4), and transferred in Tube 2. R1 was rinsed with HPLC mobile phase (Vial 5) and the solution was also transferred to Tube 2. The solution in Tube 2 was thoroughly mixed by bubbling $N_2$ for 10 seconds and injected into the HPLC for purification. HPLC condition: Phenomenex Luna (2) C18 column, 250×10 mm, 5 μm. Mobile phase: 40% ACN in 0.1% TFA. Flow rate: 4 mL/min. The labeled intermediate was eluted at about 12-14 minutes. The intermediate was collected in the dilution flask containing 30 mL water, and passed through an Oasis HLB light cartridge (pre-conditioned with 5 mL of ethanol, 10 mL of air, and 10 mL of water). The trapped intermediate was rinsed with 6 mL water (Vial 14), and eluted with 1.0 mL of absolute ethanol (Vial 13) to R2 through V35.

The eluted intermediate was heated to 60° C. under $N_2$ flow and vacuum for 3 minutes to remove ethanol. NaOH in Vial 10 was added to the dried residue. The resulting solution was heated at 45° C. for 10 minutes. HCl solution in Vial 9 was added, the content was transferred through valve 16 (V16) and an in-line sterile filter to the product vial. The product was analyzed by HPLC: Waters BEH Amide column (150*4.6 mm), 3.5 μm. Using 90%-50% D in 8 min. C: 95% water+5% ACN with 0.1% $NH_4OH$; D: 95% ACN+5% water with 0.1% $NH_4OH$. The product peak eluted at about 5 minutes. Generally, 6-[18F]fluororhamnose was synthesized in 18-25% radiochemical yield (uncorrected, n>3), radiochemical purity >95%. The synthesis time was about 90 minutes.

Example 5

Synthesis of 3-deoxy-3-F-Rhamnose (3R,4R,5S,6S)-4-(benzyloxy)-2-methoxy-6-methyl-tetrahydro-2H-pyran-3,5-diol

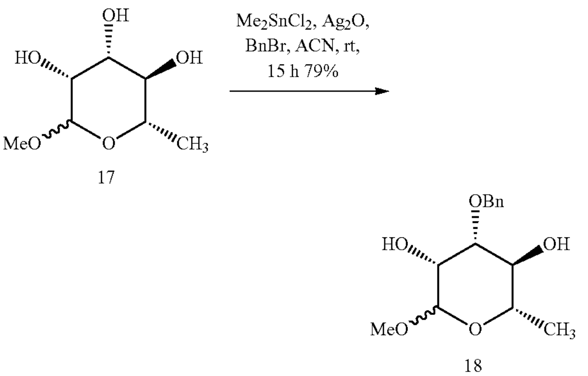

17

18

Methyl-rhamnopyranoside 17 (2.85 g, 16.0 mmol), benzyl bromide (2.91 mL, 24 mmol), dimethyltin dichloride (351 mg, 1.6 mmol) and $Ag_2O$ (4.07 g, 17.6 mmol) were stirred in anhydrous acetonitrile (90 mL) at room temperature for 15 hours. After filtered through a celite pad, the filtrate was evaporated and the residue was purified by silica gel flash chromatography to afford 18 as a colorless oil (3.41 g, 79%, α:β1).

β-isomer: $^1$H NMR (400 MHz, $CDCl_3$) δ 7.30-7.32 (m, 5H), 4.71 (d, 1H, J=1.6 Hz), 4.70 (d, 1H, J=11.3 Hz), 4.57 (d, 1H, J=11.3 Hz), 4.02 (dd, 1H, J=1.6 and 3.1 Hz), 3.67-3.61 (m, 2H), 3.56 (m, 1H), 3.36 (s, 3H), 1.32 (d, J=6.3 Hz, 3H).

α-isomer: $^1$H NMR (400 MHz, $CDCl_3$) δ 7.39-7.32 (m, 5H), 4.75 (d, 1H, J=11.3 Hz), 4.74 (s, 1H), 4.52 (d, 1H, J=11.7 Hz), 3.72-3.68 (m, 2H), 3.60 (m, 1H), 3.42 (t, 1H, J=9.0 Hz), 3.35 (s, 3H), 1.34 (d, J=6.3 Hz, 3H).

(3R,4R,5S,6S)-4-(benzyloxy)-5-hydroxy-6-methyl-tetrahydro-2H-pyran-2,3-diyldiacetate

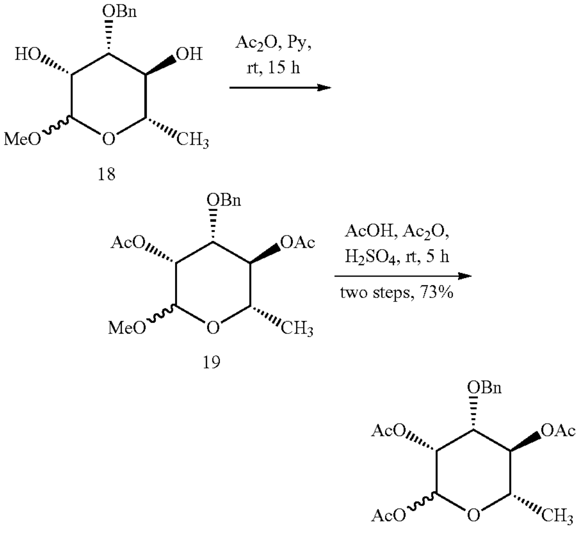

18 19 20

Compound 18 (3.24 g, 12.1 mmol) was dissolved in anhydrous pyridine (12 mL) and $Ac_2O$ (7 mL). The solution was stirred at room temperature for 15 hours. Solvents were evaporated and the residue was dissolved in EtOAc (300 mL), washed with saturated $NaHCO_3$, 1N HCl, $H_2O$, brine and dried over $Na_2SO_4$. After evaporation of solvents, the crude product 19 was used for next step.

$H_2SO_4$ (0.6 mL) was added dropwise to a solution of 19 (4.25 g, 12.1 mmol) in $Ac_2O$ (20 mL) and the solution was stirred at room temperature for 5 hours. The reaction mixture was poured into a stirred mixture of ethyl acetate (150 mL) and saturated $NaHCO_3$ (80 mL). The organic phase was separated and washed with saturated $NaHCO_3$, brine and dried over $Na_2SO_4$. After evaporation of solvents, the residue was purified by silica gel flash chromatography to afford the product 20 as a colorless oil (3.37 g, 73%).

$^1$H NMR (400 MHz, $CDCl_3$): δ 7.37-7.26 (m, 5H), 6.12 (d, 0.27H, J=2.0 Hz), 6.03 (d, 0.73H, J=2.0 Hz), 5.34 (dd, 0.73H, J=2.0 and 3.5 Hz), 5.23 (m, 0.27H), 5.16 (m, 0.27H), 5.07 (t, 0.73H, J=9.0 Hz), 4.72-4.43 (m, 2H), 3.94-3.79 (m, 2H), 2.16 (s, 2.19H), 2.12 (s, 0.81H), 2.11 (s, 2.19H), 2.10 (s, 0.81H), 2.05 (s, 0.81H), 2.04 (s, 2.19H), 1.23 (d, J=6.3 Hz, 0.81H), 1.21 (d, J=6.3 Hz, 2.19H).

(3R,4R,5R,6S)-4-hydroxy-6-methyltetrahydro-2H-pyran-2,3,5-triyl Triacetate

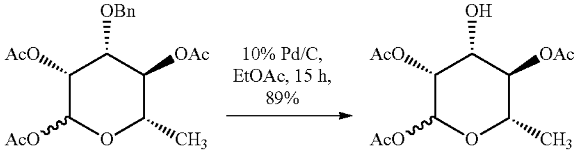

20 21

10% Pd/C (1.5 g) was added to 20 (3.15 g, 8.28 mmol) in EtOAc (200 mL). The mixture was stirred at room temperature under $H_2$ atmosphere for 2 hours and filtered through a celite pad. The filtrate was evaporated and the residue was purified by silica gel flash chromatography to afford 21 as a white solid (2.14 g, 89%).

$^1$H NMR (400 MHz, $CDCl_3$): δ 6.10 (d, 0.26H, J=2.0 Hz), 6.06 (d, 0.74H, J=1.6 Hz), 5.25 (dd, 0.26H, J=3.1 and 9.8 Hz), 5.17 (m, 0.26H), 5.09 (dd, 0.74H, J=1.8 and 13.7 Hz), 4.90 (t, 0.74H, J=9.8 Hz), 4.10-4.00 (m, 1H), 3.97-3.84 (m, 1H), 2.16 (s, 2.22H), 2.12 (s, 0.78H), 2.11 (s, 2.22H), 2.10 (s, 0.78H), 2.05 (s, 0.78H), 2.04 (s, 2.22H), 1.23 (d, J=6.3 Hz, 0.78H), 1.21 (d, J=6.3 Hz, 2.22H).

(3R,4R,5S,6S)-6-methyl-4-(((trifluoromethyl)sulfonyl)oxy)tetrahydro-2H-pyran-2,3,5-triyl Triacetate

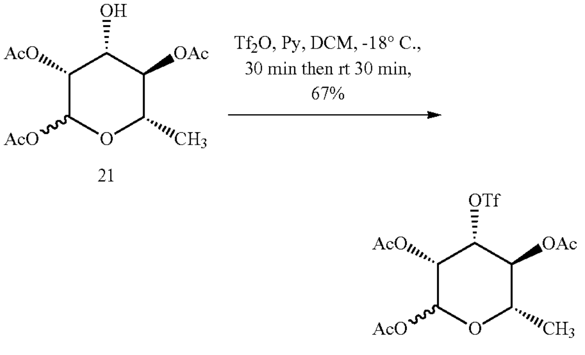

21 22

Trifluoromethanesulfonic anhydride (0.33 mL, 1.94 mmol) was added to a mixture of compound 21 (508 mg, 1.75 mmol) and pyridine (0.22 mL) in dichloromethane (18 mL) at −18° C. After stirring for 0.5 hours, the mixture was warmed up to room temperature and stirred for additional 0.5 hours. Water (50 mL) was added and the organic layer was separated. The aqueous layer was extracted with dichloromethane (3×50 mL). The combined organic layers were washed with 10% $H_2SO_4$, saturated $NaHCO_3$, brine and dried over $MgSO_4$. After evaporation of solvents, the residue was purified by silica gel flash chromatography to afford the product 22 as a colorless oil (494 mg, 67%).

$^1$H NMR (400 MHz, $CDCl_3$): δ 6.06 (d, 1H, J=2.0 Hz), 5.38 (dd, 1H, J=2.0 and 3.5 Hz), 5.28 (t, 1H, J=9.8 Hz), 5.18 (dd, 1H, J=3.7 and 10.0 Hz), 3.92 (m, 1H), 2.21 (s, 3H), 2.18 (s, 3H), 2.15 (s, 3H), 1.27 (d, J=6.3 Hz, 3H). $^{19}$F NMR (376 MHz, $CDCl_3$): δ −75.0.

(3R,4S,5R,6S)-4-hydroxy-6-methyltetrahydro-2H-pyran-2,3,5-triyl Triacetate

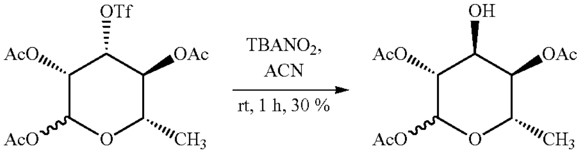

22 23

Compound 22 (422 mg, 1.0 mmol) was dissolved in dry $CH_3CN$ (2 mL) and solid tetrabutylammonium nitrite (1.44 g, 5 mmol) was added. After stirring for 1 hour at room temperature, the reaction mixture was evaporated. The residue was dissolved in $CH_2Cl_2$, washed with brine and dried over $MgSO_4$. After evaporation of solvents, the residue was purified by silica gel flash chromatography to afford the product 23 as a white solid (87 mg, 30%).

$^1$H NMR (400 MHz, $CDCl_3$): δ 5.95 (d, 0.84H, J=2.3 Hz), 5.91 (s, 0.16H), 5.10 (m, 0.16H), 5.02 (dd, 0.16H, J=1.6 and 3.5 Hz), 5.00 (dd, 0.84H, J=2.3 and 4.3 Hz), 4.89 (dd, 0.84H, J=3.3 and 8.8 Hz), 4.27 (m, 0.84H), 4.12-4.06 (m, 1H), 3.74 (m, 0.16H), 2.15 (s, 0.48H), 2.13 (s, 0.84×6H), 2.12 (s, 0.84×3H), 2.11 (s, 0.48H), 2.10 (s, 0.48H), 1.33 (d, J=6.7 Hz, 0.48H), 1.25 (d, J=6.7 Hz, 0.84×3H).

(3R,4S,5S,6S)-6-methyl-4-(((trifluoromethyl)sulfonyl)oxy)tetrahydro-2H-pyran-2,3,5-triyl Triacetate

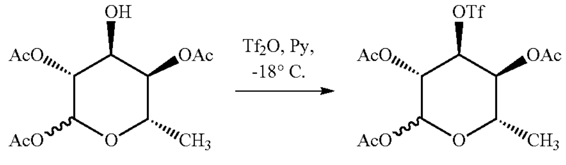

23 24

Compound 23 is treated with trifluoromethanesulfonic anhydride and pyridine to make compound 24 according to the method previously described with respect to the synthesis of compound 22.

(3S,4R,5S,6S)-4-fluoro-6-methyltetrahydro-2H-pyran-2,3,5-triyl Triacetate

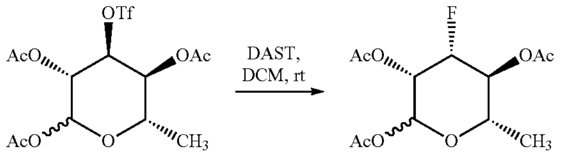

24 25

Compound 24 is treated with DAST to make compound 25 according to the method previously described with respect to the synthesis of compound 14.

(3S,4R,5S,6S)-4-fluoro-6-methyltetrahydro-2H-pyran-2,3,5-triol

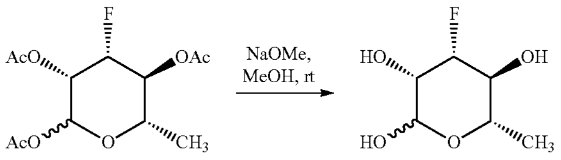

25 26

Compound 25 is treated with NaOMe to make compound 26 according to the method previously described with respect to the synthesis of compound 15.

Example 6

Radiosynthesis of 3-deoxy-3-[$^{18}$F]-fluororhamnose 3-deoxy-3-[$^{18}$F]-fluororhamnose is synthesized from compound 24 using the method previously described, such as in Examples 2 and 4.

Example 7

Synthesis of (3R,4R,5S,6R)-5-(((2S,3R,4S,5S,6R)-3-[$^{18}$F]-fluoro-4,5-dihydroxy-6-(hydroxymethyl)tetrahydro-2H-pyran-2-yl)oxy)-6-(hydroxymethyl)tetrahydro-2H-pyran-2,3,4-triol)

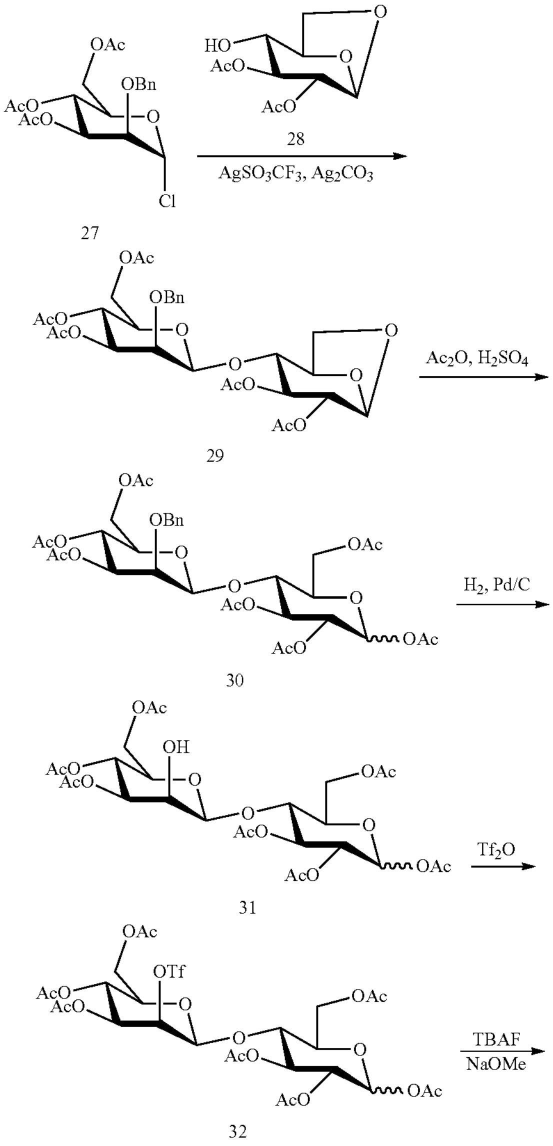

27 28 29 30 31 32

-continued

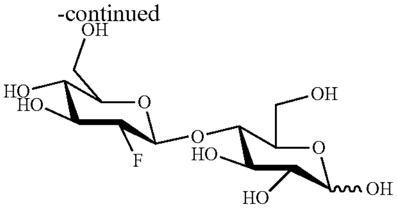

33

(3R,4R,5S,6R)-5-(((2S,3R,4S,5S,6R)-3[$^{18}$F]-fluoro-4,5-dihydroxy-6-(hydroxymethyl)tetrahydro-2H-pyran-2-yl)oxy)-6-(hydroxymethyl)tetrahydro-2H-pyran-2,3,4-triol 8-deoxy-8[$^{18}$F]-fluorocellobiose 8-deoxy-8[$^{18}$F]-fluorocellobiose is synthesized from compound 32 using the methods described herein.

(2R,3R,4S,5S,6S)-2-(Acetoxymethyl)-5-(benzyloxy)-6-(((1R,2R,3S,4R)-3,4-diacetoxy-6,8-dioxabicyclo[3.2.1]octan-2-yl)oxy)tetrahydro-2H-pyran-3,4-diyl Diacetate (29)

A solution of compound 27 in anhydrous ether is added slowly to a stirred solution of compound 28 in anhydrous acetonitrile containing silver trifluoromethanesulfonate ($CF_3SO_3Ag$), silver carbonate ($Ag_2CO_3$) and powdered drierite. The resulting mixture is stirred at room temperature and filtered through celite. The residue is washed with $CH_2Cl_2$. The combined filtrates are evaporated and the residue is purified by silica gel flash chromatography to produce compound 29.

(3R,4S,5R,6R)-6-(Acetoxymethyl)-5-(((2S,3S,4S,5R,6R)-4,5-diacetoxy-6-(acetoxymethyl)-3-(benzyloxy)tetrahydro-2H-pyran-2-yl)oxy)tetrahydro-2H-pyran-2,3,4-triyl Triacetate (30)

Compound 29 is treated with $Ac_2O$ and $H_2SO_4$ to make compound 30, using the method previously described in the synthesis of compound 20.

(3R,4S,5R,6R)-6-(Acetoxymethyl)-5-(((2S,3S,4R,5R,6R)-4,5-diacetoxy-6-(acetoxymethyl)-3-hydroxytetrahydro-2H-pyran-2-yl)oxy)tetrahydro-2H-pyran-2,3,4-triyl Triacetate (31)

Compound 30 is treated with 10% Pd/C and $H_2$ to make compound 31, using the method previously described in the synthesis of compound 21.

(3R,4S,5R,6R)-6-(Acetoxymethyl)-5-(((2S,3S,4S,5R,6R)-4,5-diacetoxy-6-(acetoxymethyl)-3-(((trifluoromethyl)sulfonyl)oxy)tetrahydro-2H-pyran-2-yl)oxy)tetrahydro-2H-pyran-2,3,4-triyl Triacetate (32)

Compound 31 is treated with trifluoromethanesulfonic anhydride and pyridine to make compound 32, using the method previously described in the synthesis of compound 22.

(3R,4R,5S,6R)-5-(((2S,3R,4S,5S,6R)-3-Fluoro-4,5-dihydroxy-6-(hydroxymethyl)tetrahydro-2H-pyran-2-yl)oxy)-6-(hydroxymethyl)tetrahydro-2H-pyran-2,3,4-triol (33)

n-$Bu_4NF$ is added to a solution of compound 32 in anhydrous acetonitrile. The reaction mixture is stirred at room temperature, concentrated and the residue is purified by flash chromatography on a silica gel column to give the intermediate product which is treated with NaOMe to produce compound 33, using the method previously described in the synthesis of compound 15.

Example 8

Synthesis of (2S,3R,4S,5S,6R)-2-(((2R,3S,4S,5R,6R)-5-[$^{18}$F]-fluoro-4,6-dihydroxy-2-(hydroxymethyl)tetrahydro-2H-pyran-3-yl)oxy)-6-(hydroxymethyl)tetrahydro-2H-pyran-3,4,5-triol)

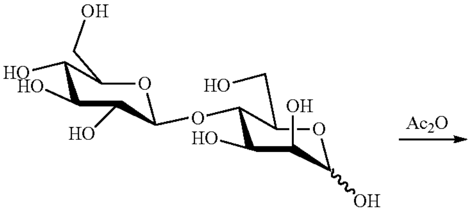

34

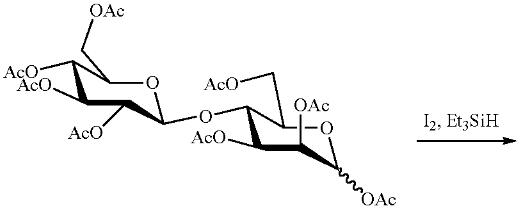

35

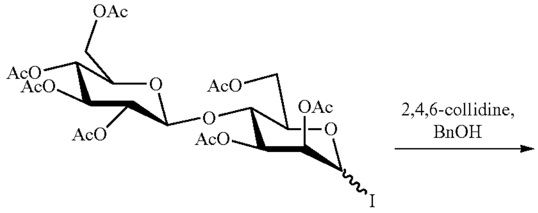

36

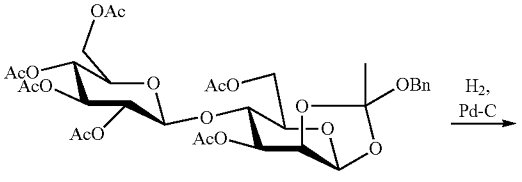

37

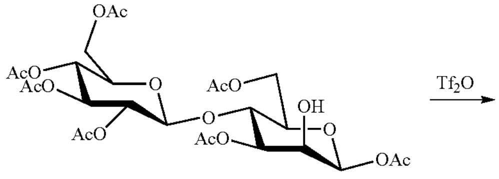

38

-continued

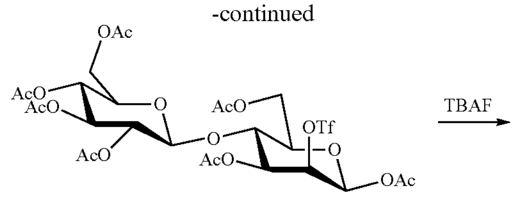

39

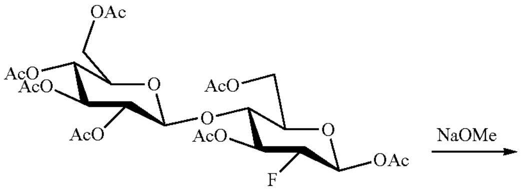

40

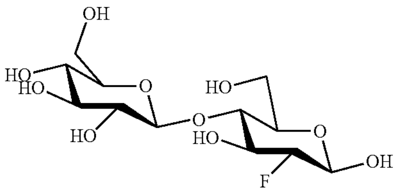

41

(3S,4S,5R,6R)-6-(Acetoxymethyl)-5-(((2S,3R,4S,5R,6R)-3,4,5-triacetoxy-6-(acetoxymethyl) tetrahydro-2H-pyran-2-yl)oxy)tetrahydro-2H-pyran-2,3,4-triyl Triacetate (35)

Compound 34 is treated with $Ac_2O$ and pyridine to make compound 35, using the method previously described in the synthesis of compound 19.

(2R,3R,4S,5R,6S)-2-(Acetoxymethyl)-6-(((2R,3R,4S,5S,6R)-4,5-diacetoxy-2-(acetoxymethyl)-6-iodo-tetrahydro-2H-pyran-3-yl)oxy)tetrahydro-2H-pyran-3,4,5-triyl Triacetate (36)

Iodine and triethylsilane are sequentially added to a solution of compound 35 in dichloromethane. The reaction is stirred at reflux temperature until TLC analysis indicates that the reaction is substantially complete. After cooling to room temperature, the mixture is diluted with dichloromethane and washed with a solution of saturated sodium hydrogen carbonate containing sodium thiosulfate for reducing the residual amount of iodine. The aqueous phase is extracted with dichloromethane, and the collected organic phase is dried with sodium sulfate and concentrated to provide the crude product 36 for next step.

(2S,3R,4S,5R,6R)-2-(((3aS,5R,6R,7S,7aS)-7-Acetoxy-5-(acetoxymethyl)-2-(benzyloxy)-2-methyltetrahydro-5H-[1,3]dioxolo[4,5-b]pyran-6-yl)oxy)-6-(acetoxymethyl)tetrahydro-2H-pyran-3,4,5-triyl Triacetate (37)

Freshly activated 4 Å molecular sieves are added to the residue, and the mixture is suspended in anhydrous dichloromethane. 2,4,6-collidine and BnOH are then added, and the mixture is stirred at room temperature. The mixture is filtered through a short pad of silica gel, and the residue from the filtered liquor is purified by silica gel flash chromatography to afford the product 37.

(2R,3R,4S,5R,6S)-2-(Acetoxymethyl)-6-(((2R,3R,4R,5S,6S)-4,6-diacetoxy-2-(acetoxymethyl)-5-hydroxytetrahydro-2H-pyran-3-yl)oxy)tetrahydro-2H-pyran-3,4,5-triyl Triacetate (38)

Compound 37 is treated with 10% Pd/C and $H_2$ to make compound 38, using the method previously described in the synthesis of compound 21.

(2R,3R,4S,5R,6S)-2-(Acetoxymethyl)-6-(((2R,3R,4S,5S,6S)-4,6-diacetoxy-2-(acetoxymethyl)-5-(((trifluoromethyl)sulfonyl)oxy)tetrahydro-2H-pyran-3-yl)oxy)tetrahydro-2H-pyran-3,4,5-triol Triacetate (39)

Compound 38 is treated with trifluoromethanesulfonic anhydride and pyridine to make compound 39, using the method previously described in the synthesis of compound 22.

(2R,3R,4S,5R,6S)-2-(Acetoxymethyl)-6-(((2R,3R,4S,5R,6S)-4,6-diacetoxy-2-(acetoxymethyl)-5-fluorotetrahydro-2H-pyran-3-yl)oxy)tetrahydro-2H-pyran-3,4,5-triyl Triacetate (40)

Compound 39 is treated with n-$Bu_4NF$ to make compound 40, using the method previously described in the synthesis of compound 33.

(2S,3R,4S,5S,6R)-2-(((2R,3S,4S,5R,6R)-5-Fluoro-4,6-dihydroxy-2-(hydroxymethyl) tetrahydro-2H-pyran-3-yl)oxy)-6-(hydroxymethyl)tetrahydro-2H-pyran-3,4,5-triol (41)

Compound 40 is treated with NaOMe to make compound 41 using the method previously described in the synthesis of compound 15.

(2S,3R,4S,5S,6R)-2-(((2R,3S,4S,5R,6R)-5-[$^{18}$F]-fluoro-4,6-dihydroxy-2-(hydroxymethyl)tetrahydro-2H-pyran-3-yl)oxy)-6-(hydroxymethyl)tetrahydro-2H-pyran-3,4,5-triol 2-2[$^{18}$F]-fluorocellobiose 2-deoxy-2[$^{18}$F]-fluorocellobiose is synthesized from compound 39 using the methods described herein.

Example 9

L-Rhamnose as a Marker for Fungal Infection

L-Rhamnose uptake is low in bacteria (gram negative and gram positive) and very low in *P. aeruginosa* and macrophages (Ordonez et al., *J. Nucl Med,* 58: 144-50, 2017). L-Rhamnose is metabolized in *Aspergillus* species by alpha-rhamnosidases. Fungi such as *Aspergillus* use a nonphosphorylative pathway where L-Rhamnose is first oxidized to L-rhamno-g-lactone by L-rhamnose-1-dehydrogenase (LRA1). This intermediate is then converted to L-rhamnonate by L-rhamnono-g-lactonase (LRA2) and subsequently to L-2-keto-3-deoxyrhamnonate by L-rhamnonate dehydratase (LRA3). This is then cleaved into pyruvate and L-lactaldehyde by L-2-keto-3-deoxyrhamnonate (Watanabe et al., *Febs J,* 275:5139-49, 2008; Watanabe et al., *J. Biol Chem,* 283:20372-82, 2008).

Figure 1D:
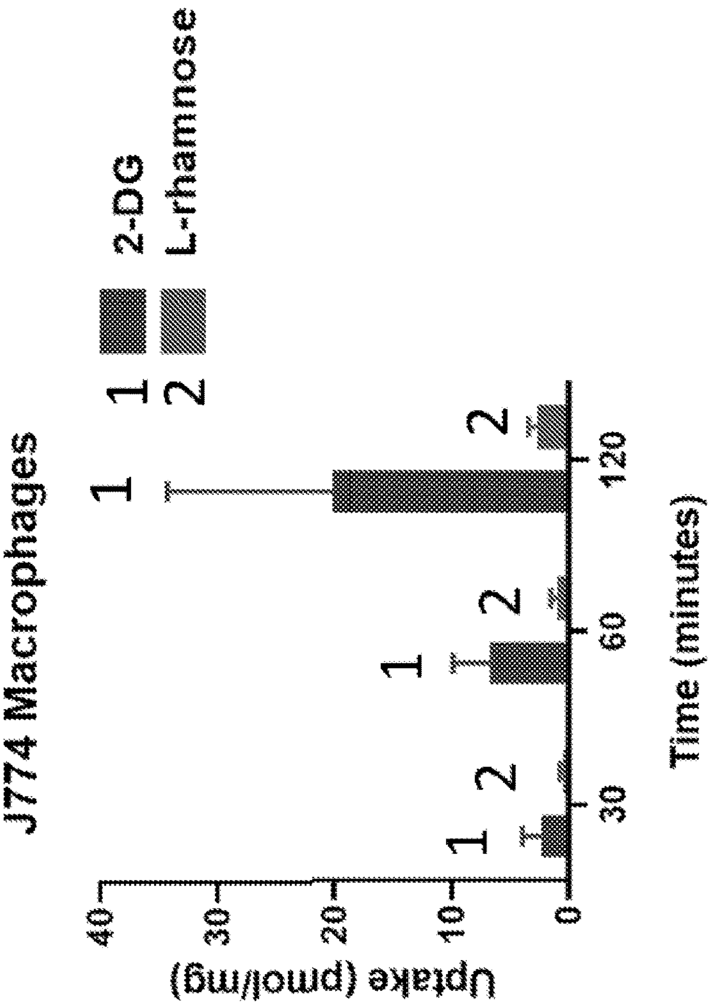
Figure 1C:
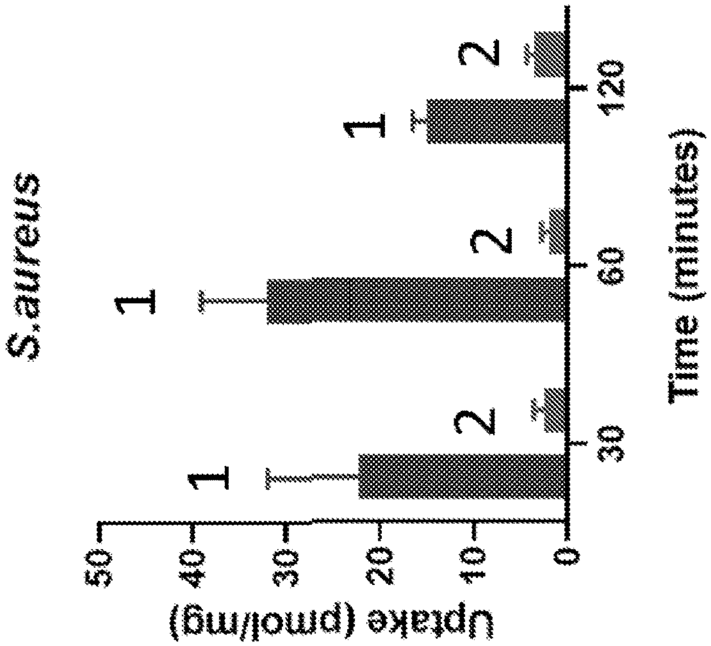
Figure 1E:
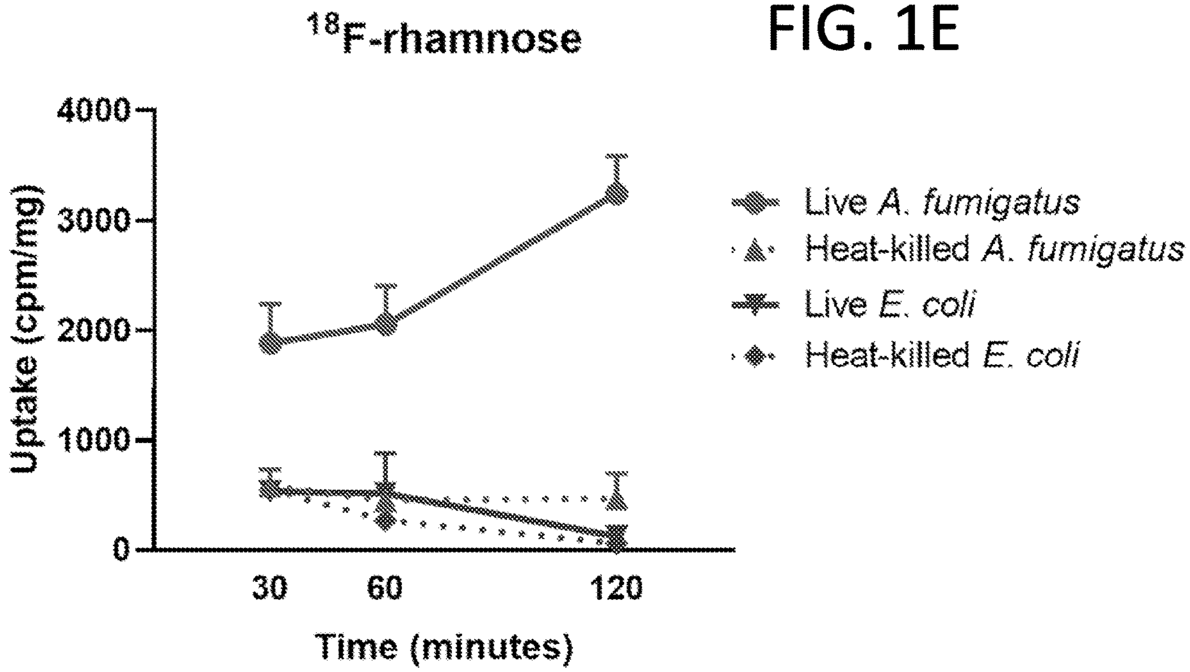
Figure 1F:
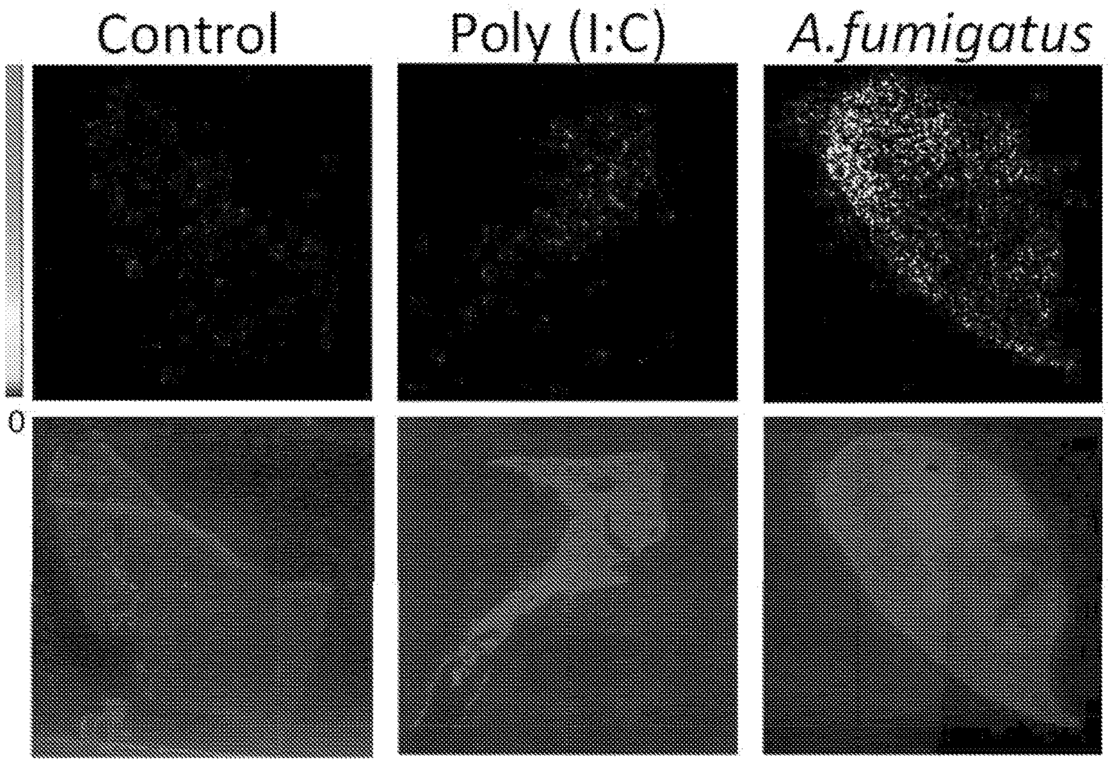
Figure 2:
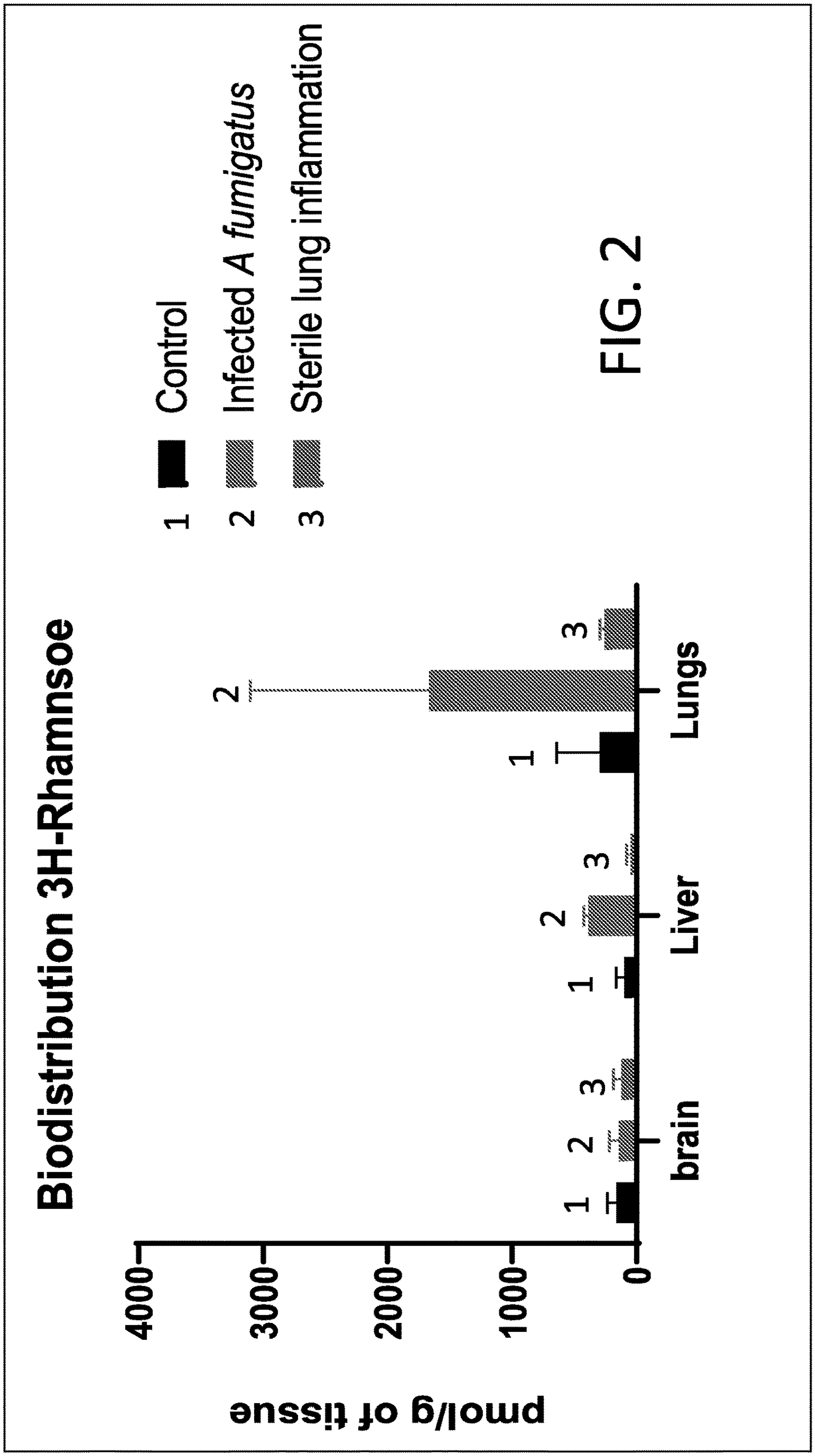
FIG. 2 is a bar graph showing $^{3}H$-L-Rhamnose results from biodistribution studies showing increased uptake in the lungs of infected compared to control mice and mice with sterile lung inflammation.

Radiolabeled L-Rhamnose was tested as a fungal-specific ligand. In vitro uptake assays using 3H-L-Rhamnose (in vitro incubation of $^{3}$H-L-Rhamnose with different cultures of *Aspergillus, Rhizomucor, Cryptococcus*, bacteria and macrophages followed by culture washing and measurement of retained radioactivity) showed significant retention of the sugar by *A. fumigatus* (FIG. 1A), while minimal retention was seen with bacteria and macrophages (FIGS. 1B-1D).

ex vivo experiments were performed, including biodistribution (injecting the animals with radiolabeled molecules followed by euthanasia, collection of organs and measurement of radioactivity) and autoradiography (sectioning of lung tissues from injected animals to measure residual radioactivity). Biodistribution studies showed uptake of $^{3}$H-L-Rhamnose in the lungs of infected animals but not in uninfected controls (FIG. 2). Autoradiography showed accumulation of $^{3}$H-L-Rhamnose in the lungs of infected but not uninfected animals (FIG. 1F).

Figure 3A:
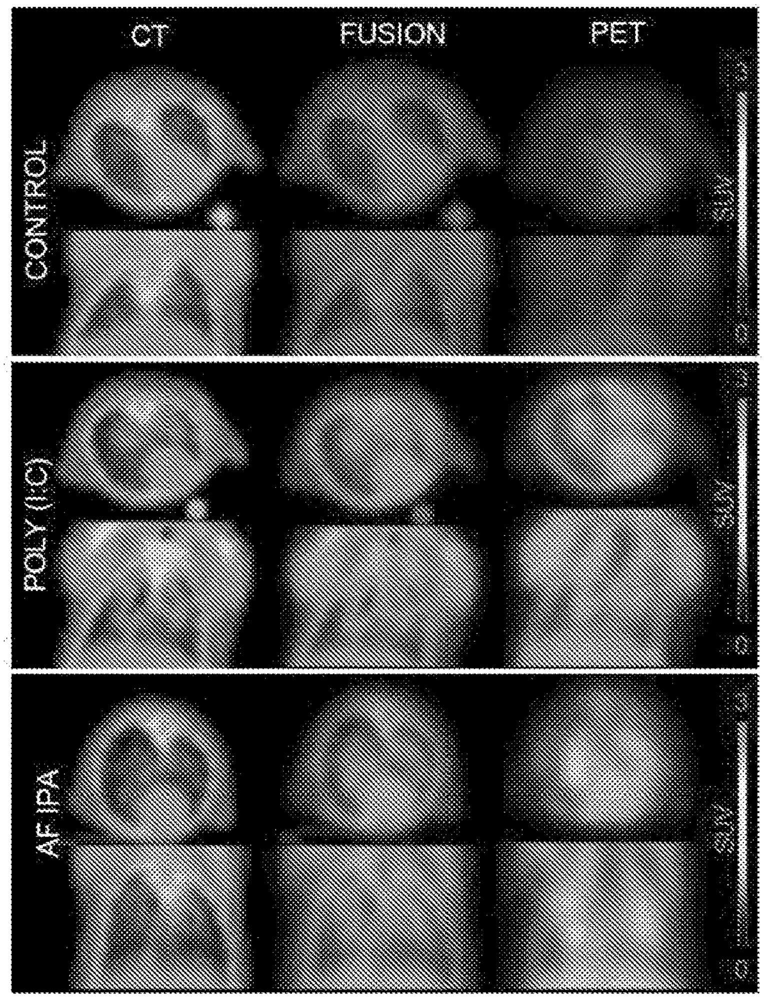
FIGS. 3A-3B.
Figure 3B:
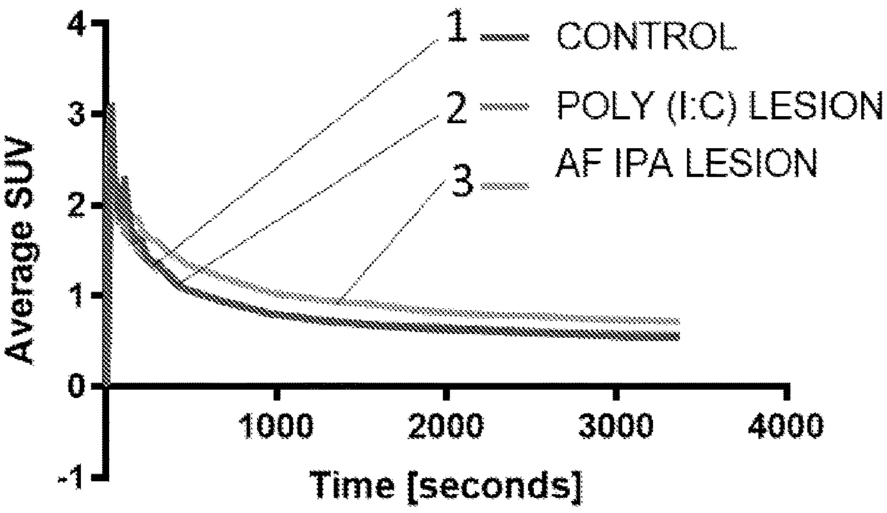

$^{18}$F-L-rhamnose PET ligand ($^{18}$F-2-deoxy-2-fluoro-L-rhamnose; radiosynthesis details provided separately by the CSC) was synthesized as described in Examples 1 and 2, and evaluated for in vitro uptake by *A. fumigatus* and *E. coli.* $^{18}$F-L-rhamnose was specifically internalized by live *A. fumigatus* cultures when compared to heat-killed cultures but not by *E. coli.* in vivo uptake of $^{18}$F-L-rhamnose was assessed by PET/CT in mouse models of pulmonary aspergillosis (2 days following post-pharyngeal inoculation with *Aspergillus* cultures). Standardized uptake values (SUVs) of $^{18}$F-L-rhamnose in infected mice were then measured, and compared to animals with sterile lung inflammation (24 hours following post-pharyngeal poly (I:C) administration) and healthy controls. In vivo PET/CT imaging with a 60-minute dynamic $^{18}$F-L-rhamnose PET/CT imaging of a pulmonary aspergillosis model showed a slight higher uptake in lung lesions compared to controls and poly (I:C) treated mice (FIG. 3A). There was however relatively fast washout of the ligand (FIG. 3B).

These results demonstrate that *A. fumigatus* selectively accumulates $^{18}$F-L-rhamnose in vitro and in vivo.

Based on these observations, $^{18}$F-L-rhamnose derivatives with the $^{18}$F located on other carbon atoms instead of C2, for example, C3 or C6, can be generated as described herein. These resulting $^{18}$F-L-rhamnose derivatives (see Examples, 3-6) can be used to detect fungi in vivo or ex vivo using the methods provided herein. For example, dynamic PET/CT imaging and delayed PET/CT imaging (acquiring 60 minutes of dynamic data after injection of the ligand, and static imaging at 120 minutes post injection) can be performed. Bolus/infusion can be used to prolong the biological half-life of the compound and increase circulation time which would result in higher uptake by the fungi.

Example 10

Cellobiose as a Marker for Fungal Infection

Cellobiose, a disaccharide (two β-glucose molecules with a 1→4 glycosidic bond), is metabolized by *Aspergillus fumigatus* β-glucosidase and has no known human metabolism. In the presence of β-glucosidase, cellobiose is metabolized into two glucose molecules resulting in uptake in the area of infection as well as release of glucose into the circulation resulting in brain uptake (cellobiose does not cross the blood brain barrier, BBB). Thus, cellobiose can be radiolabeled and used as a ligand for fungal detection.

Figure 4A:
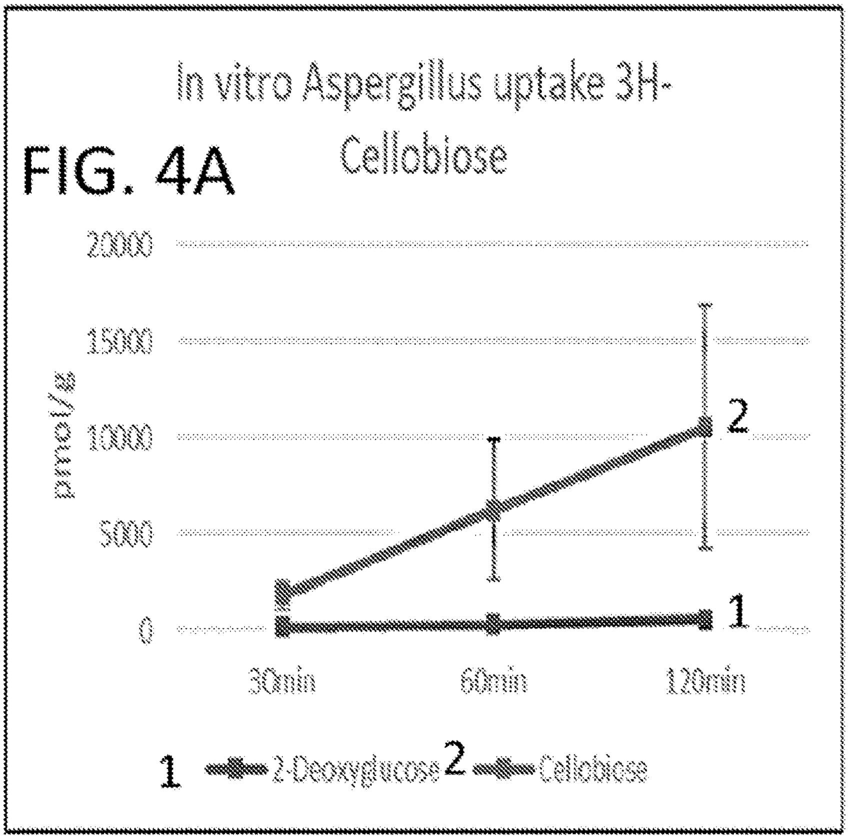
FIGS. 4A-4C. In vitro uptake of $^{3}H$-cellobiose by *Aspergillus* (FIG. 4A) but not by macrophage (J744) cell lines (FIG. 4B).
Figure 4B:
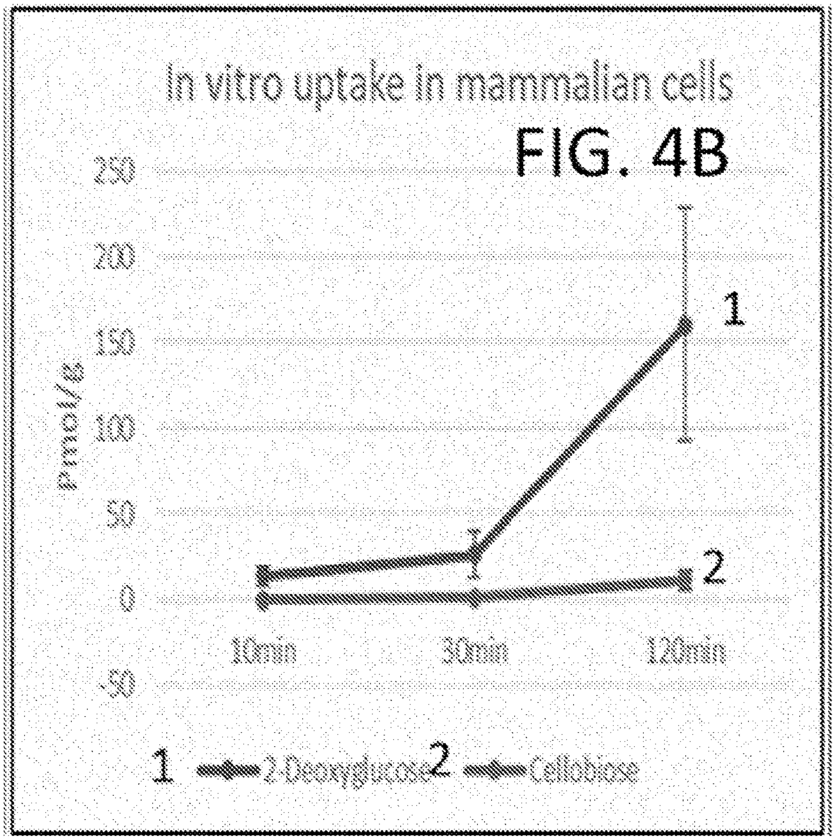

In vitro studies using $^{3}$H-cellobiose were performed with measurement of retained radioactivity after incubation and washing of the cultures using a beta counter. *A. fumigatus* had high uptake of $^{3}$H-cellobiose (>than 2-deoxyglucose uptake) in culture (FIG. 4A) while mammalian cells did not (FIG. 4B). This uptake of $^{3}$H-cellobiose in *A. fumigatus* increased over time, especially at 120 minutes.

Figure 4C:
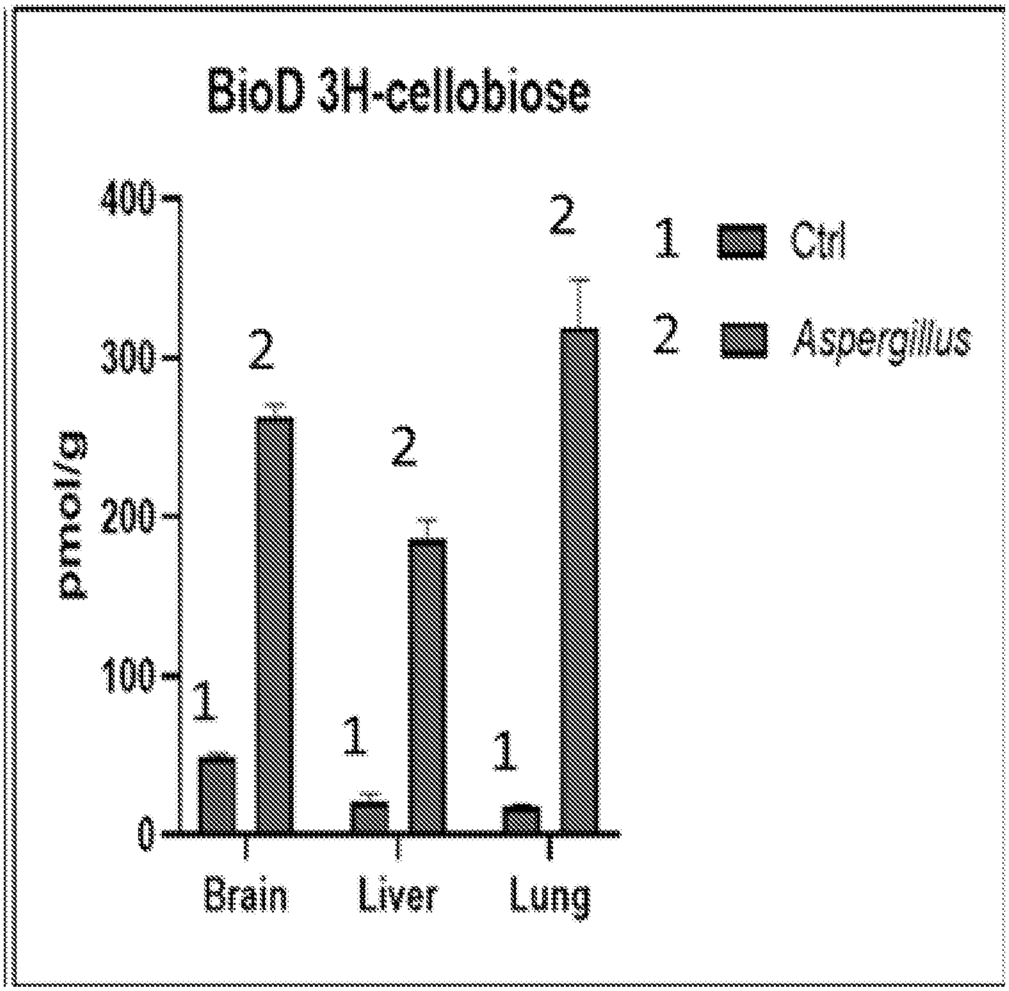

In biodistribution studies using $^{3}$H-cellobiose (animals injected with $^{3}$H-cellobiose followed by euthanasia, collection of organs and measurement of radioactivity), increased uptake in *A. fumigatus*-infected lungs (nasopharyngeal model) was found, as compared to uninfected animals (FIG. 4C). Uptake in the brain was also noted in nasopharyngeally infected animals indicating hydrolysis of $^{3}$H-cellobiose into two glucose molecules and secondary uptake of glucose molecules by brain cells.

Figures 5A, 5B:
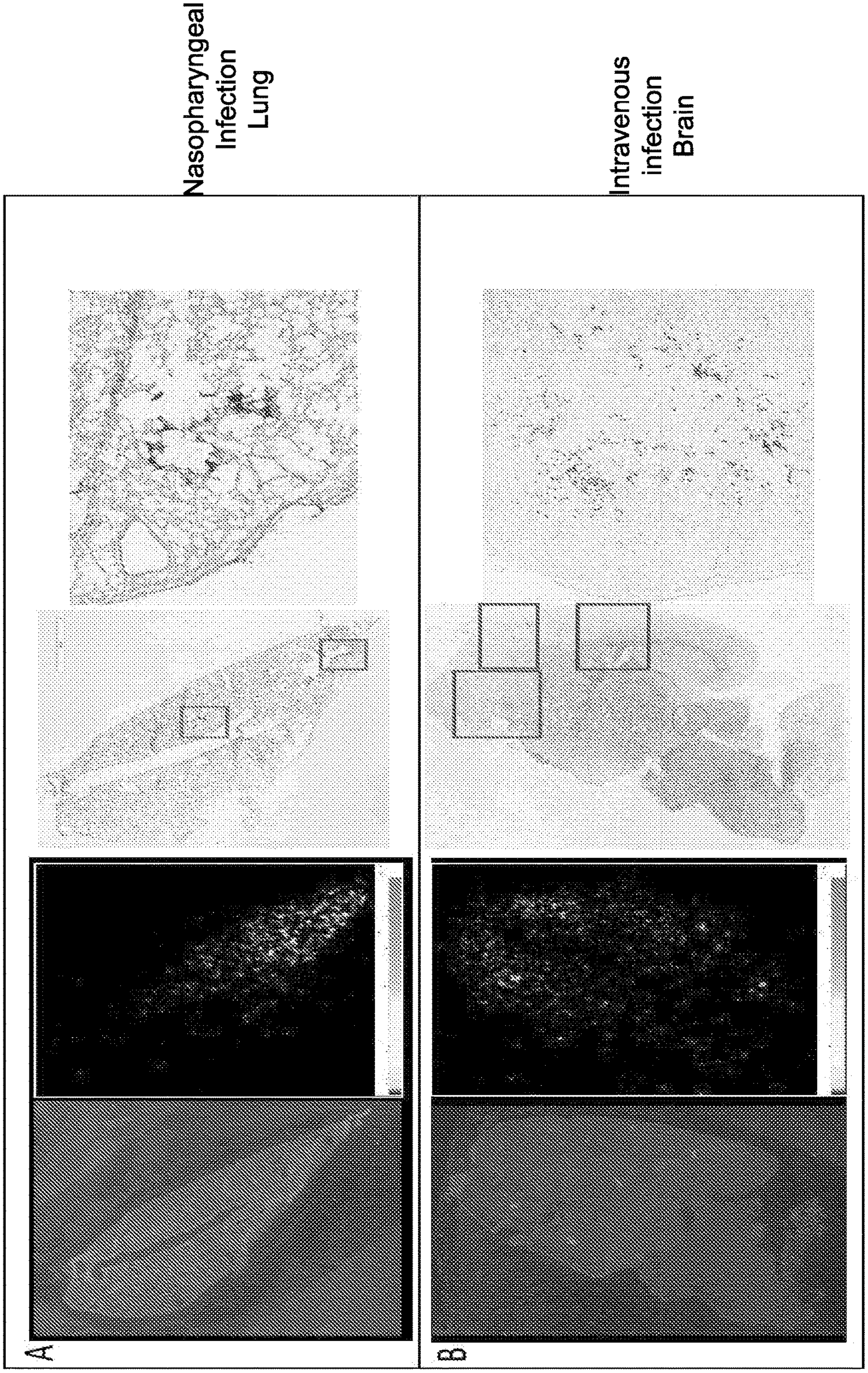
FIGS. 5A-5B: Autoradiography and GMS staining of (FIG. 5A) lung in an *Aspergillus fumigatus* nasopharyngeally-infected mouse and (FIG. 5B) brain in an *Aspergillus fumigatus* IV infected mouse. GMS staining confirms the presence of fungal hyphae with corresponding 3H-Cellobiose uptake

Uptake of $^{3}$H-cellobiose by the infected animal lungs (nasopharyngeal inoculation model) and brains (intravenous inoculation model), but not in control animals or animals with sterile lung inflammation by autoradiography (sectioning of lung tissues from injected animals to measure retained radioactivity), was observed (FIGS. 5A and 5B). Those findings were supported by GMS staining showing fungal hyphae in similar distributions to autoradiography uptake.

To demonstrate the specificity of $^{3}$H-cellobiose, in vitro screening of various bacteria can be performed with radioTLC to confirm the presence or lack of cellobiose metabolism. RadioTLC can be performed using $^{3}$H-cellobiose as a reference and the presence of labeled glucose in the cell lysate obtained following incubation with fungi or bacteria can then be determined. If the pathogen has β-glucosidase, more than one peak will be detected, indicating metabolism (glucose and downstream metabolites); if the pathogen does not have β-glucosidase, only one peak representing the parent molecule (cellobiose), is detected. Radio-TLC can be used to evaluate plasma from control mice to further confirm the lack of mammalian metabolism for cellobiose: if β-glucosidase is expressed in the mouse, more than one peak will be detected, indicating metabolism (glucose and downstream metabolites) but if the enzyme is not present, as expected, only radiolabeled cellobiose will be detected.

Figure 6:
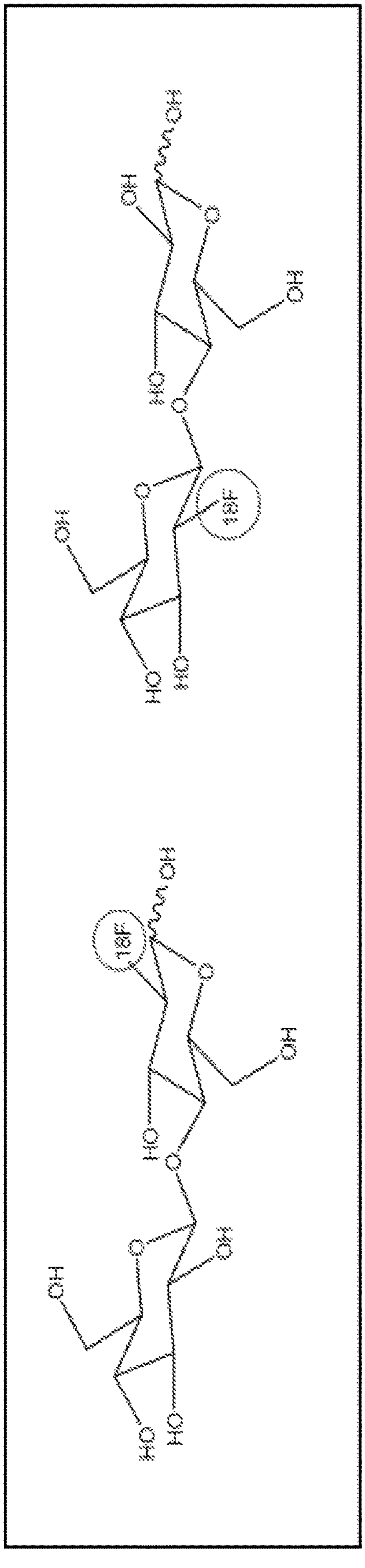
FIG. 6: $^{18}F$-deoxycellobiose with the isotope located on C2 of the first glucose molecule or on the C2 of the second glucose molecule.

Radiosynthesis of labeled cellobiose can be achieved with $^{18}$F located on one of the carbon atoms on the cellobiose molecule, for example, on C2 in the first or second glucose molecule (FIG. 6; see Examples 7 and 8). The in vitro uptake of both $^{18}$F-cellobiose molecules can be measured as described herein and used for in vivo PET imaging as described herein. Since the resulting molecule is essentially FDG (after breaking the 1→4 glycosidic bond by β-glucosidase), this will result in uptake, phosphorylation and entrapment of $^{18}$F-cellobiose metabolites in areas with fungal infection.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of detecting a fungus, comprising:

contacting the fungus with a compound having a structure

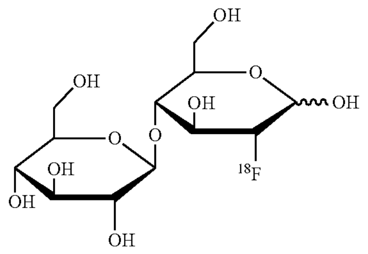

thereby detecting the fungus;

wherein the fungus is an *Aspergillus* or Mucormycete.

2. The method of claim 1, wherein the fungus is an *Aspergillus*.

3. The method of claim 1, wherein the method is an in vivo method of detecting a fungal infection in a subject, and the contacting comprises administering the compound to a subject, and the method further comprises subsequently performing diagnostic imaging of the subject, thereby detecting the fungal infection in the subject.

4. The method of claim 3, wherein the diagnostic imaging of the subject comprises positron emission tomography (PET).

5. The method of claim 3, wherein the subject is undergoing treatment of the fungal infection, and the method monitors the treatment.

6. The method of claim 1, wherein the fungus is *A. fumigatus, A. flavus, A. terreus*, or *A. niger.*

7. The method of claim 1, wherein the fungus is *A. fumigatus.*

8. The method of claim 1, wherein the fungus is a Mucormycetes.

* * * * *